(12) United States Patent
Heilek et al.

(10) Patent No.: US 8,461,383 B2
(45) Date of Patent: Jun. 11, 2013

(54) PROCESS FOR STARTING UP A SEPARATING PROCESS FOR PURIFYING REMOVAL OF ACRYLIC ACID CRYSTALS FROM A SUSPENSION S OF CRYSTALS THEREOF IN MOTHER LIQUOR

(75) Inventors: Joerg Heilek, Bammental (DE); Dirk Litters, Lampertheim (DE); Klaus Joachim Mueller-Engel, Stutensee (DE)

(73) Assignee: BASF SE, Ludwigshafen (DE)

( * ) Notice: Subject to any disclaimer, the term of this patent is extended or adjusted under 35 U.S.C. 154(b) by 338 days.

(21) Appl. No.: 12/897,199

(22) Filed: Oct. 4, 2010

(65) Prior Publication Data

US 2011/0124834 A1     May 26, 2011

Related U.S. Application Data

(60) Provisional application No. 61/356,078, filed on Jun. 18, 2010, provisional application No. 61/252,181, filed on Oct. 16, 2009.

(30) Foreign Application Priority Data

Oct. 16, 2009  (DE) .......................... 10 2009 045 767
Jun. 18, 2010  (DE) .......................... 10 2010 030 279

(51) Int. Cl.
*C07C 51/43*     (2006.01)

(52) U.S. Cl.
USPC ........................................................ 562/600

(58) Field of Classification Search
CPC ...................................................... C07C 51/43
USPC ...................................................... 562/600
IPC ...................................................... C07C 51/43
See application file for complete search history.

(56) References Cited

U.S. PATENT DOCUMENTS

| | | | |
|---|---|---|---|
| 6,382,313 B2 | 5/2002 | Mitsumoto et al. | |
| 7,112,695 B2 * | 9/2006 | Eck et al. ....................... | 562/600 |
| 2009/0018347 A1 | 1/2009 | Heilek et al. | |
| 2010/0206821 A1 | 8/2010 | Heilek et al. | |

FOREIGN PATENT DOCUMENTS

| | | |
|---|---|---|
| DE | 100 36 881 A1 | 2/2002 |
| DE | 102 28 859 A1 | 1/2004 |
| DE | 102 43 625 A1 | 4/2004 |
| DE | 103 23 758 A1 | 12/2004 |
| DE | 10 2006 045 089 A1 | 3/2008 |
| DE | 10 2007 004 960 A1 | 7/2008 |
| DE | 10 2007 043 748 A1 | 9/2008 |
| DE | 10 2007 043 759 A1 | 9/2008 |
| DE | 10 2007 043 758 A1 | 10/2008 |
| DE | 10 2007 028 332 A1 | 12/2008 |
| DE | 10 2007 028 333 A1 | 12/2008 |
| DE | 10 2009 000 987 A1 | 4/2010 |
| DE | 10 2008 054 587 A1 | 6/2010 |
| EP | 0 492 400 A1 | 7/1992 |
| EP | 1 079 194 A2 | 2/2001 |
| EP | 1 232 004 | 8/2002 |
| EP | 1 448 282 | 8/2004 |
| WO | WO 01/32301 A1 | 5/2001 |
| WO | WO 01/77056 A1 | 10/2001 |
| WO | WO 02/09839 A1 | 2/2002 |
| WO | WO 02/055469 A1 | 7/2002 |
| WO | WO 03/041832 A1 | 5/2003 |
| WO | WO 03/041833 | 5/2003 |
| WO | WO 03/078378 A1 | 9/2003 |
| WO | WO 2004/035514 A1 | 4/2004 |
| WO | WO 2006/111565 A2 | 10/2006 |
| WO | WO 2008/090190 A1 | 7/2008 |
| WO | WO 2010/094637 A1 | 8/2010 |

* cited by examiner

*Primary Examiner* — Paul A Zucker
(74) *Attorney, Agent, or Firm* — Oblon, Spivak, McClelland, Maier & Neustadt, L.L.P.

(57) ABSTRACT

A process for starting up a separating process for purifying removal of acrylic acid crystals from a suspension S of crystals thereof in mother liquor with a hydraulic wash column which has a crystal melt circuit including crystal melt space, and a process space and a distributor space which are separated by an end with passages connecting the two spaces, in which the crystal bed is formed for the first time by first filling the crystal melt circuit and, at least partly, the process space with an acrylic acid-comprising startup liquid whose acrylic acid crystal formation temperature is less than or equal to the temperature of the suspension S increased by 15° C., and then continuing the filling of the wash column with the suspension S and optionally with control liquor until the difference between the pressure in the crystal melt space and the pressure in the distributor space falls suddenly, the arithmetic mean of the total waste liquor flow flowing through the filters of the filter tubes of the wash column until this time, based on the area of all filters, being not more than 80 m$^3$/(m$^2$·h).

41 Claims, 3 Drawing Sheets

PROCESS FOR STARTING UP A SEPARATING PROCESS FOR PURIFYING REMOVAL OF ACRYLIC ACID CRYSTALS FROM A SUSPENSION S OF CRYSTALS THEREOF IN MOTHER LIQUOR

The present invention relates to a process for starting up a separating process for purifying removal of acrylic acid crystals from a suspension S of crystals thereof in mother liquor with an apparatus which comprises a hydraulic wash column which has a process space which is rotationally symmetric with respect to its longitudinal axis running from the top downward and is bounded by a cylindrical outer wall and two opposite ends on the axis of symmetry, in which one or more filter tubes extend through the process space from the upper end of the process space parallel to the longitudinal axis thereof, which run toward the lower end of the process space opposite the upper end, and have, in the half of the process space toward the lower end of the process space, at least one filter F which constitutes the only direct connection between the particular filter tube interior and the process space, and are conducted out of the wash column outside the process space, the quotient Q=L/D of the distance L between the upper and lower ends of the process space and the diameter D of the process space is 0.3 to 4, the lower end of the process space is followed in the downward direction by the crystal melt space of the wash column, a rotatable removal device being integrated between the two spaces and a crystal melt circuit which is conducted through the crystal melt space comprising, outside the crystal melt space, a delivery pump P1 which is outside the wash column and has a suction side and a pressure side, a first delivery connection G1 which leads from the crystal melt space of the wash column to the suction side of the delivery pump P1, a second delivery connection G2 which leads from the pressure side of the delivery pump P1 back into the crystal melt space of the wash column and has an outlet A from the crystal melt circuit with regulable flow, and a heat transferer W, through which either the delivery connection G1 from the crystal melt space to the suction side of the delivery pump P1 or the delivery connection G2 from the pressure side of the delivery pump P1 to the crystal melt space is conducted, connected upstream of the upper end of the process space in the upward direction is a distributor space which is separated from the process space at least by one end B which has passages U which lead into the process space on the side of the end B facing the process space and into the distributor space on the side of the end B facing away from the process space, a delivery pump P2 which has a suction side and a pressure side and a source QS of the suspension S are present outside the wash column, a first delivery connection E1 leading from the source QS to the suction side of the delivery pump P2, and a second delivery connection E2 leading from the pressure side of the delivery pump P2 into the distributor space, a delivery pump P3 which has a suction side and a pressure side and a source QT of a control liquor are optionally present outside the wash column, a first delivery connection C1 leading from the suction side of the pump P3 to the source QT, and a second delivery connection C2 leading from the pressure side of the pump P3 into the distributor space and/or into the longitudinal section of the process space between the upper end thereof and the filters F of the filter tubes, and in which, in the course of performance of the separating process, in steady-state operation thereof, the pump P2 is used to continuously conduct a stream ST of the suspension S from the source QS through the delivery connections E1, E2 via the distributor space and through the passages U into the process space of the wash column, optionally, the pump P3 is used to conduct a stream SL of the control liquor from the source QT through the delivery connections C1, C2 via the distributor space and the passages U and/or directly into the process space of the wash column, overall, a stream SM comprising mother liquor and optionally control liquor is conducted as waste liquor stream into the filter tube interior via the filters F of the filter tubes, and out of the wash column via the filter tubes, and this waste liquor stream SM conducted out of the wash column is used as the source QT for the control liquor, the conduction of mother liquor and optionally control liquor in the process space of the wash column maintains the development of a crystal bed of acrylic acid crystals which has a buildup front facing the upper end of the process space (the buildup front refers to the transition from the crystal suspension to the (compacted) crystal bed and is characterized by a relatively abrupt rise in the crystal content per unit volume), at which crystals of the stream ST of the suspension S (of the suspension stream) supplied are added continuously onto the crystal bed, the crystal bed is conveyed from the top downward past the filters F toward the rotating removal device by the force which results from the hydraulic flow pressure drop of the conduction of mother liquor and optionally control liquor in the process space, the rotating removal device removes acrylic acid crystals from the crystal bed which meets it, the stream of the acrylic acid crystals removed is conveyed through the rotating removal device and/or past the rotating removal device into the crystal melt space which follows downstream of the process space in conveying direction of the crystal bed, and melted in the crystal melt circuit conducted through the crystal melt space (frequently also referred to in simplified terms merely as "melt circuit") as a result of introduction of heat with the heat transferer W to give a crystal melt stream, and the flow through the outlet A is regulated such that, based on the flow rate of the aforementioned crystal melt stream, proceeding from the crystal melt space, a substream of crystal melt flows as wash melt stream through the rotating removal device and/or past the rotating removal device against the direction of movement of the crystal bed back into the process space, where it ascends within the crystal bed conveyed downward and in doing so washes the mother liquor off the crystals and forces it back, said mother liquor remaining in the crystal bed having been conveyed with the latter under the filters F, which forms, in the longitudinal section of the process space which extends from the filters F to the lower end of the process space, in the crystal bed, a wash front which divides the crystal bed, from the top downward, into a mother liquor zone and into a wash melt zone, and the remaining substream of the aforementioned crystal melt stream leaves the crystal melt circuit through the outlet A.

Acrylic acid, either itself or in the form of its salts or its esters, is of significance especially for preparation of polymers for a wide variety of different fields of use (for example adhesives, superabsorbents, binders).

In the synthesis of acrylic acid, it is typically not obtained as a pure product but as part of a substance mixture which, as well as the target compound desired in high purity, also comprises undesired constituents, for example solvents, starting compounds and by-products. This substance mixture is frequently a liquid.

For example, acrylic acid is obtainable by catalytic gas phase oxidation of glycerol, propane, propene and/or acrolein. These starting compounds are diluted in the gas phase, generally with inert gases such as molecular nitrogen, $CO_2$ and/or steam, passed in a mixture with molecular oxygen at elevated temperatures and optionally elevated pressure over transition metal mixed oxide catalysts, and converted oxidatively to a product gas mixture comprising acrylic acid.

By means of condensative and/or absorptive measures, the acrylic acid is subsequently typically converted to the liquid (condensed) phase, in the course of which a basic removal of the acrylic acid from the compounds which accompany it in the product gas mixture is already achieved.

Using a wide variety of different combinations of thermal separating processes (useful such processes include, for example, rectification, extraction, stripping, distillation, desorption, etc.), the acrylic acid is finally removed in high purity from the aforementioned liquid phases. A constituent of such process combinations is in many cases the process of suspension crystallization.

When a substance mixture comprising acrylic acid and present in its liquid state is cooled, and the formation of crystals of acrylic acid is brought about in doing so, suspension crystallization is one possible process for removing the acrylic acid from the substance mixture.

This exploits the fact that, as the crystals which form from the acrylic acid grow, the constituents which are present in the liquid substance mixture alongside acrylic acid are frequently displaced from the crystal lattice and remain in the mother liquor (the term "mother liquor" shall be understood in this document such that it comprises both melts (therein, a proportion by weight of $\geq 50\%$ by weight is accounted for by the acrylic acid) composed of acrylic acid and impurities, and solutions of acrylic acid and impurities which may accompany it in solvents or in solvent mixtures (therein, the acrylic acid accounts for a proportion by weight of $<50\%$ by weight), with the proviso that the acrylic acid crystallizes out in the course of cooling thereof (i.e. in the course of cooling of the mother liquor)).

Sometimes, high-purity crystals of acrylic acid are already obtained in a one-stage suspension crystallization process. If required, the suspension crystallization can also be performed in more than one stage.

The process of suspension crystallization for crystallative removal of acrylic acid is known (cf., for example, DE-A 10 2007 043758, DE-A 10 2007 043748, DE-A 10 2007 004960, DE-A 10 2007 043759 and DE 10 2009 000987.6).

Appropriately in application terms, it is performed with the aid of an indirect heat transferer (cooler or crystallizer) having a secondary space and at least one primary space.

As a result of the transfer of heat from the liquid substance mixture which comprises acrylic acid and is fed to the secondary space (and generally flows through it) through the material dividing wall (the heat transfer surface) which separates the secondary space and the at least one primary space from one another into a coolant which flows within the at least one primary space, the liquid substance mixture is cooled until its saturation limit with acrylic acid is exceeded and the liquid substance mixture counteracts oversaturation by formation (by deposition) of crystals formed from acrylic acid.

When the desired degree of crystallization (the term "degree of crystallization" here means the mass fraction or else proportion by mass of the fine crystals present in the resulting suspension of crystals of acrylic acid in mother liquor remaining (in liquid form) in the total mass of the crystal suspension) has been attained, the crystal suspension is conducted out of the secondary space.

By removing the acrylic acid crystals formed from the mother liquor, the acrylic acid can be isolated in corresponding purity from the crystal suspension.

A crucial step which has a major influence on the purity of the acrylic acid removed is the separating process employed for the removal of the acrylic acid crystals from the mother liquor which comprises the constituents other than acrylic acid in enriched form and the as yet uncrystallized proportions of the acrylic acid. This separating process may have more than one stage, in which case a removal with a hydraulic wash column is frequently preferably employed at least in the last stage.

The removal with a hydraulic wash column may, however, also constitute the only separating stage. In principle, the task of the removal with a hydraulic wash column is to very substantially quantitatively separate the contaminated mother liquor from the acrylic acid crystals.

Separating processes for purifying removal of acrylic acid crystals from a suspension of crystals thereof in mother liquor with the aid of a hydraulic wash column are known (cf., for example, DE 10 2009 000987.6, WO 2006/111565, DE-A 10 2007 004960, EP-A 1 448 282, US-A 2009/018347, WO 03/041832, WO 01/77056, WO 04/35514, WO 03/41833, WO 02/9839, DE-A 100 36 881, WO 02/55469, WO 03/78378 and the prior art cited in these documents).

An example of a hydraulic wash column (0) is shown in FIG. 1 of this document. It has a process space (B) which is rotationally symmetric with respect to its longitudinal axis running from the top downward (all alphabetical or numerical addresses placed between brackets in this document relate to the figures appended to this document).

This process space is bounded by a cylindrical outer wall (28) and two opposite ends on the axis of symmetry, one or more filter tubes (6) extending through the process space (B) from the upper end (29) of the process space (B) parallel to the longitudinal axis thereof, which run toward the lower end (30) of the process space (B) opposite the upper end (without penetrating it), and have, in the half of the process space (B) toward the lower end of the process space (B), at least one filter F (7) which constitutes the only direct connection between the particular filter tube interior and the process space (B), and are conducted out of the wash column (0) outside the process space (B).

The lower end of the process space (B) is followed in the downward direction by the crystal melt space (C) of the hydraulic wash column (0), a rotatable removal device (16) being integrated between the two spaces and a crystal melt circuit (31) being conducted through the crystal melt space (C).

The removal device (16) is normally secured to a drive shaft (18) which is driven about its longitudinal axis by a drive unit for rotation, which imparts the torque required for the rotation of the removal device (16) thereto.

The crystal melt circuit (31) comprises, outside the crystal melt space (C), a delivery pump P1 (11) which is outside the wash column (0) and has a suction side and a pressure side. A first delivery connection G1 (5) leads from the crystal melt space (C) of the wash column (0) via a heat transferer W (9) to the suction side of the delivery pump P1 (11). A second delivery connection G2 (12) leads from the pressure side of the delivery pump P1 (11) back into the crystal melt space (C) of the wash column (0). It comprises an outlet A (3) with a regulable (10) flow.

Connected upstream of the upper end of the process space (B) in the upward direction is a distributor space (A) which is separated from the process space (B) at least by one end B (32) which has passages U (26) which lead into the process space (B) on the side of the end B facing the process space and into the distributor space (A) on the side of the end B facing away from the process space (B).

Outside the hydraulic wash column (0) there is a delivery pump P2 (8) which has a suction side and a pressure side. A first delivery connection E1 (33) leads from a source QS (1) of the suspension of the acrylic acid crystals in mother liquor to the suction side of the delivery pump P2 (8). A second delivery connection E2 (34) leads from the pressure side of the delivery pump P2 (8) into the distributor space (A) of the hydraulic wash column (0).

Outside the wash column (0) there is generally (but not necessarily) additionally a delivery pump P3 (13) which has a suction side and a pressure side. A first delivery connection C1 (35) leads from the suction side of the pump P3 (13) to a source QT for what is known as control liquor (the control liquor used is waste liquor conducted out (removed) via the at least one filter tube (6) (cf., for example, WO 2006/111565)).

A second delivery connection (36) leads from the pressure side of the pump P3 (13) into the distributor space (A) of the hydraulic wash column (0) and/or into the longitudinal section of the process space (B) between the upper end (29) thereof and the at least one filter (7) of the at least one filter tube (6).

In the course of performance of the removal process, in steady-state operation thereof, the pump P2 (8) is used to continuously conduct a stream of the suspension of crystals of acrylic acid in mother liquor through the delivery connections E1 (33), E2 (34) via the distributor space (A) and through the passages U (26) into the process space (B) of the wash column (0) (optionally, the pump P3 (13) is additionally used to conduct control liquor through the delivery connections C1 (35), C2 (36) via the distributor space (A) and through the passages U (26) and/or directly into the process space of the wash column (0)). The passages U (26) work toward a very homogeneous distribution of the crystal suspension over the cross section of the process space (B). The pressure conditions in the filter tube interior and in the process space (B) are configured such that a stream comprising mother liquor and optionally control liquor is conducted as waste liquor stream into the filter tube interior via the filters F (7) of the filter tubes (6), and out of the wash column (0) (via a corresponding outlet) (2) via the filter tubes (6) (generally via a waste liquor collecting space (27) which may be integrated, for example, into the end B).

This waste liquor stream forms the source QT of an optionally additionally used control liquor stream.

The conduction of mother liquor and optionally control liquor in the process space of the wash column (0) (first from the top downward and then with superimposed crossflow through the filters (7) into the filter tubes (6)) constantly sustains the development, which occurred for the first time when the separating process was started up, of a (compacted) "crystal bed (filtercake) (4)" of acrylic acid crystals and thus maintains the development of a crystal bed (4) of acrylic acid crystals which has a buildup front (25) facing the upper end of the process space, at which crystals of the supplied stream of the suspension of acrylic acid crystals in mother liquor are added continuously onto the (compacted) crystal bed filtercake (4) (in the literature, the buildup front is frequently also referred to as the filtration front).

The force resulting from the hydraulic flow pressure drop of the mother liquor and optionally control liquor on the flow path thereof in the process space (B) through the crystal bed (4) compacts the crystal bed (4) and conveys it from the top downward past the filters F (7) (effectively as the filtercake of the cross-filtration) toward the rotating removal device (16).

The rotating removal device (16) continuously removes acrylic acid crystals from the crystal bed (4) which meets it. The stream of removed acrylic acid crystals which thus arises is, according to the configuration of the rotating removal device (16), conveyed through the latter and/or past the latter into the crystal melt space (C) which follows downstream of the process space (B) in conveying direction of the crystal bed (4), and melted in the crystal melt circuit (31) (or melt circuit (31)) conducted through the crystal melt space (C) as a result of introduction of heat with the heat transferer W (9) to give a crystal melt stream (of course, the heat transferer W for this purpose may alternatively also be integrated into the delivery connection G2; it is also possible for this purpose for more than one heat transferer to be integrated into the crystal melt circuit).

The flow through the outlet A (3) is regulated (10) such that, based on the flow rate of the aforementioned crystal melt stream, proceeding from the crystal melt space (C), a substream of the specifically comparatively lighter (having a lower density) crystal melt which has been displaced by the crystals conveyed into the crystal melt space flows as wash melt stream, according to the configuration of the rotating removal device (16), through the latter and/or past the latter against the direction of movement of the crystal bed (4) back into the process space (B) (the ascending wash melt mass flow will not normally be greater than the crystal mass flow conducted into the process space (B) via the crystal suspension), where it ascends within the crystal bed (4) conveyed downward and in doing so washes the mother liquor off the crystals while forcing the mother liquor back upward, said mother liquor remaining in the crystal bed (4) having been conveyed with the latter under the filters F (7), which forms, in the longitudinal section of the process space (B) which extends from the filters F (7) to the lower end of the process space (30), in the crystal bed (4), a wash front (37) which divides the crystal bed, from the top downward, into a mother liquor zone (extends from the wash front (37) to the buildup front) and into a wash melt zone (extends from the wash front (37) to the lower end of the crystal bed (4)), and the remaining substream of the aforementioned crystal melt stream leaves the melt circuit (31) through the outlet A (3) (the delivery pump P1 (11) functions as a pure circulation pump).

In other words, by virtue of the wash melt which flows in the opposite direction to the conveying direction of the crystal bed (4), the crystal bed (4) impregnated only with a residual amount of mother liquor below the filters F (7) is virtually forced into the wash melt flowing upward in the process space (B) (and vice versa) as a result, and, as a washing effect (further possible washing effects are detailed on page 9 of WO 01/77056), the mother liquor which remains in the crystal bed (4) in the course of "filtration" is simply forced back to a limited degree by the wash melt. Given appropriate adjustment of the wash melt flow to the boundary conditions of the removal process, a steady state is established, such that a so-called wash front (37) is established at a defined height in the process space (B) (in fact a substantially stable "phase boundary" between wash melt (pure melt) and mother liquor). The wash front is defined as that height in the section of the process space (B) which extends from the lower end of the crystal bed to the upper filter edge at which, viewed over the process space height, the highest temperature and concentration gradients occur.

Above and below the wash front (37), the level-dependent temperatures (concentrations) substantially comparatively rapidly (generally within a change in level (referred to as "wash front region") of less than ±5 cm) reach a value which no longer changes as a function of height in each case.

This value in the region above the wash front (37) is essentially the temperature (the corresponding concentration) of the suspension of acrylic acid crystals in mother liquor supplied to the process space (B), and that in the region below the wash front (37) the melting point temperature (the corresponding concentration) of the wash melt (pure melt). The height position of the wash front (37) can be varied to a limited degree by regulating the ratio of crystal mass flow conveyed within the process space to wash melt flow conveyed in the opposite direction. Below a particular minimum length of the wash melt zone, the washing effect (the removal effect) becomes better with increasing length of the wash melt zone. Appropriately in application terms, the wash front (37) is 50 to 200 mm, often up to 100 mm, below the lower filter edge (below the lower edge of the filters F (7)).

To start up the separating process for purifying removal of acrylic acid crystals from the suspension thereof in mother liquor, which is to be performed in the steady state as described above, WO 01/77056 recommends feeding the appropriate crystal suspension directly into the unfilled hydraulic wash column and at first removing only mother liquor through the filters of the filter tubes until a fixed crystal bed has developed in the desired bed height in the process space of the wash column. Subsequently, removal device and crystal melt circuit are put into operation and, after a certain initial phase with the flow through the outlet of the crystal melt circuit closed, the latter is regulated so as to result in the desired position of the wash front.

However, a disadvantage of this method of startup is that it is accompanied by blockage of the crystal melt circuit with a frequency of economic relevance. This is generally attributable to the fact that, in the case of direct feeding of the crystal suspension into the unfilled hydraulic wash column, crystals already get into the crystal melt circuit to an enhanced degree until the time at which the desired bed height is attained. When the crystal melt circuit is then put into operation, the crystals which have settled out beforehand (which have undergone essentially no compaction) are stirred up abruptly, which can result in the blockage described (especially considering that the delivery pump for the crystal melt circuit (the melt circuit pump) attains its full delivery performance only after a certain warmup time).

In principle, the above-described phenomenon can be counteracted by, in the course of startup of the hydraulic wash column, first filling the melt circuit comprising the crystal melt space and the process space of the previously unfilled wash column with an acrylic acid-comprising startup liquid such that the fill height of the startup liquid in the process space at least overtops the removal device, and only then continuing the filling of the hydraulic wash column with crystal suspension and optionally waste liquor as control liquor.

In the case of hydraulic wash columns whose quotient $Q=L/D$ of the distance L between the upper and lower ends of the process space and the diameter D of the process space is 0.3 to 4, and in the case of such a procedure, however, working pressures which led to bursting of the bursting disk incorporated within this region for safety reasons occurred in the course of further operation of the separating process with comparatively high regularity and after only relatively short operating times in the region comprising the delivery connection E2 and the distributor space.

It was an object of the present invention, in view of the problems described, to provide a suitable remedy.

Figure 1:
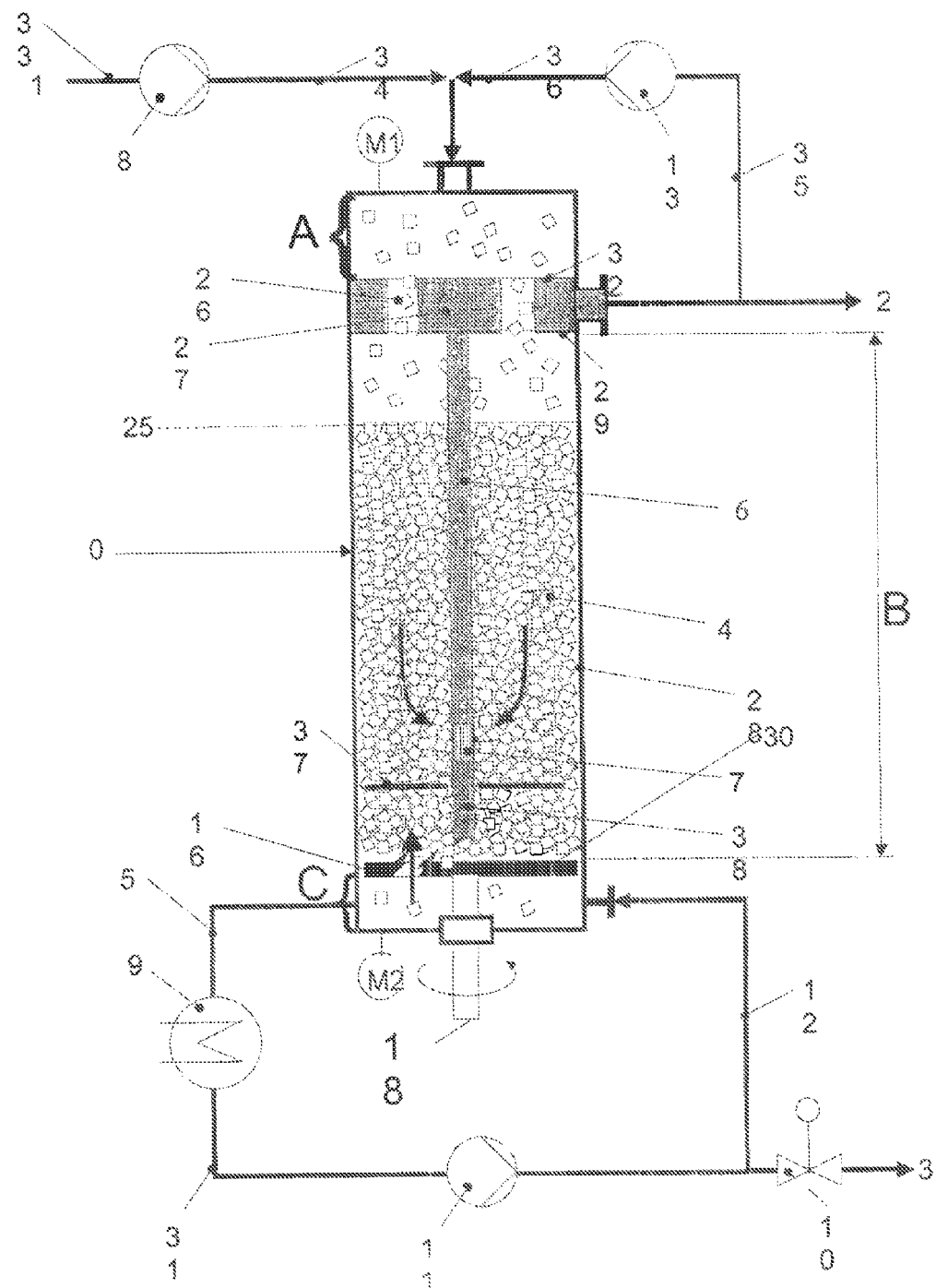
FIG. 1 is a cross-sectional view schematically showing an example of hydraulic wash column.

Accordingly, a process is provided for starting up a separating process for purifying removal of acrylic acid crystals from a suspension S of crystals thereof in mother liquor with an apparatus which comprises a hydraulic wash column which has a process space which is rotationally symmetric with respect to its longitudinal axis running from the top downward and is bounded by a cylindrical outer wall and two opposite ends on the axis of symmetry, in which one or more filter tubes extend through the process space from the upper end of the process space parallel to the longitudinal axis thereof, which run toward the lower end of the process space opposite the upper end (without penetrating it), and have, in the half of the process space toward the lower end of the process space, at least one filter F which constitutes the only direct connection between the particular filter tube interior and the process space, and are conducted out of the wash column outside the process space, the quotient $Q=L/D$ of the distance L between the upper and lower ends of the process space and the diameter D of the process space is 0.3 to 4, the lower end of the process space is followed in the downward direction by the crystal melt space of the wash column, a rotatable removal device being integrated between the two spaces and a crystal melt circuit which is conducted through the crystal melt space comprising, outside the crystal melt space, a delivery pump P1 which is outside the wash column and has a suction side and a pressure side, a first delivery connection G1 which leads from the crystal melt space of the wash column to the suction side of the delivery pump P1, a second delivery connection G2 which leads from the pressure side of the delivery pump P1 back into the crystal melt space of the wash column and has an outlet A from the melt circuit with regulable flow, and a heat transferer W, through which either the delivery connection G1 from the crystal melt space to the suction side of the delivery pump P1 or the delivery connection G2 from the pressure side of the delivery pump P1 to the crystal melt space is conducted, connected upstream of the upper end of the process space in the upward direction is a distributor space which is separated from the process space at least by one end B which has passages U which lead into the process space on the side of the end B facing the process space and into the distributor space on the side of the end B facing away from the process space, a delivery pump P2 which has a suction side and a pressure side and a source QS of the suspension S are present outside the wash column, a first delivery connection E1 leading from the source QS to the suction side of the delivery pump P2, and a second delivery connection E2 leading from the pressure side of the delivery pump P2 into the distributor space, delivery pump P3 which has a suction side and a pressure side and a source QT of a control liquor are optionally present outside the wash column, a first delivery connection C1 leading from the suction side of the pump P3 to the source QT, and a second delivery connection C2 leading from the pressure side of the pump P3 into the distributor space and/or into the longitudinal section of the process space between the upper end thereof and the filters F of the filter tubes, and in which, in the course of performance of the separating process, in steady-state operation thereof, the pump P2 is used to continuously conduct a stream ST of the suspension S from the source QS through the delivery connections E1, E2 via the distributor space and through the passages U into the process space of the wash column, optionally, the pump P3 is used to conduct a stream SL of the control liquor from the source QT through the delivery connections C1, C2 via the distributor space and the passages U and/or directly into the process space of the wash column, overall, a stream SM comprising mother liquor and optionally control liquor is conducted as waste liquor stream into the filter tube interior via the filters F of the filter tubes, and out of the wash column via the filter tubes, and this waste liquor stream SM conducted out of the wash column is used as the source QT for the control liquor, the conduction of mother liquor and optionally control liquor in the process space of the wash column maintains the development of a crystal bed of acrylic acid crystals which has a buildup front facing the upper end of the process space, at which crystals of the stream ST of the suspension S supplied are added continuously onto the crystal bed, the crystal bed is conveyed from the top downward past the filters F toward the rotating removal device by the force which results from the hydraulic flow pressure drop of the conduction of mother liquor and optionally control liquor in the process space, the rotating removal device removes acrylic acid crystals from the crystal bed which meets it, the stream of the acrylic acid crystals removed is conveyed through the rotating removal device and/or past the rotating removal device into the crystal melt space which follows downstream of the process space in conveying direction of the crystal bed, and melted in the crystal melt circuit (or melt circuit) conducted through the crystal melt space as a result of introduction of heat with the heat transferer W to give a crystal melt stream, and the flow through the outlet A is regulated such that, based on the flow rate of the aforementioned crystal melt stream, proceeding from the crystal melt space, a substream of crystal melt flows as wash melt stream through the rotating removal device and/or past the rotating removal device against the direction of movement of the crystal bed back into the process space, where it ascends within the crystal bed conveyed downward and in doing so washes the mother liquor off the crystals and forces it back, said mother liquor remaining in the crystal bed having been conveyed with the latter under the filters F, which forms, in the longitudinal section of the process space which extends from the filters F to the lower end of the process space, in the crystal bed, a wash front which divides the crystal bed, from the top downward, into a mother liquor zone and into a wash melt zone, and the remaining substream of the aforementioned crystal melt stream leaves the melt circuit through the outlet A, wherein, in the course of startup of the separating process for first development of the crystal bed in the process space, the melt circuit comprising the crystal melt space, and the process space of the previously unfilled wash column, are at first filled with an acrylic acid-comprising startup liquid AT such that the fill height of the startup liquid AT in the process space overtops at least the removal device, then the filling of the wash column is continued by using the pump P2 to conduct a stream ST* of the suspension S from the source QS through the delivery connections E1, E2 via the distributor space and through the passages U into the process space of the wash column and optionally using the pump P3 to conduct a substream of the waste liquor stream SM* conducted out of the wash column through the filter tubes as source QT*, as control liquor stream SL* through the delivery connections C1, C2 via the distributor space and the passages U and/or directly into the process space of the wash column, at least until the time $t_s$ is attained at which the pressure difference $P_D = P_K - P_V$, where $P_K$ is the pressure existing at any desired point in the crystal melt space at a particular time in the supply of the stream ST* and $P_V$ is the pressure which exists at the same time at any desired point in the distributor space, no longer rises or remains constant as a function of the duration of the supply of the stream ST*, but decreases suddenly, with the proviso that until the time $t_S$, the mean superficial velocity on the filters F, calculated as the arithmetic mean of the total waste liquor flow tubes SM* which flows at the particular time (this is the total waste liquor flow; i.e. the sum of all waste liquor flows conducted into the individual filter tubes, summed over all filter tubes) through the filters F of the filter tubes during the supply of the stream ST*, divided by the total area of all filters F, is not more than 80 m³/(m²·h), the acrylic acid-comprising startup liquid AT is one from which, in the course of cooling until crystallization sets in, the crystals which form in the course of crystallization are acrylic acid crystals, and between the crystal formation temperature $T^{KB}$, reported in degrees Celsius, of these acrylic acid crystals in the startup liquid AT and the temperature $T^S$, reported in degrees Celsius, of the suspension S of the stream ST*, the following relationship is satisfied:

$$T^{KB} \leq T^S + 15°\ C.$$

Preferably in accordance with the invention, the arithmetic mean (also referred to in this document as "mean filter superficial velocity" or as "mean superficial velocity on the filters F") of the total waste liquor flow SM* flowing through the filters F of the filter tubes at the particular time during the supply of the stream ST*, divided by the total area of all filters F until the time $t_s$, is not more than 75 and more preferably not more than 70 m³/(m²·h).

In general, the aforementioned arithmetic mean (the mean filter superficial velocity) normalized to the total area of all filters F will be at least 5 or at least 10, advantageously at least 15 and particularly advantageously at least 20 m³/(m²·h).

In other words, ranges favorable in accordance with the invention for the aforementioned arithmetic mean normalized to the total area of all filters F (the mean filter superficial velocity) are the ranges of >0 to 80 m³/(m²·h), preferably 5 to 75 m³/(m²·h), more preferably 10 to 70 m³/(m²·h), even more preferably 15 to 65 m³/(m²·h) and particularly advantageously 20 to 50 m³/(m²·h).

All of the above and all further statements in this document apply especially when the quotient Q=L/D is $\geq 0.5$ or $\geq 0.7$. Of course, all of the above and all further statements in this document also apply when L/D is $\leq 3.5$, or $\geq 3$, or $\geq 2.5$, or $\leq 2$. Quotients Q=L/D which are not too large are advantageous in accordance with the invention. This is also against the background that the friction resistance to be overcome in the course of transport of the crystal bed within the process space along the contact surface between crystal bed and inner wall of the process space, based on the volume of the crystal bed, falls with decreasing Q.

Appropriately in application terms, the distance L between the upper and lower ends of the process space will be $\geq 0.5$ m, preferably $\geq 0.8$ m and more preferably $\geq 1$ m. In general, L, however, will be $\leq 5$ m and frequently $\leq 4$ m or $\leq 3$ m.

Favorable internal diameters D of a process space of a hydraulic wash column suitable in accordance with the invention are in the range from 300 to 3000 mm, preferably in the range from 700 to 2000 mm.

Favorable process space internal volumes accessible to the crystals in the process according to the invention are 0.05 to 20 m³, advantageously 0.2 to 10 m³ and particularly advantageously 1 to 5 m³.

The area of a filter F is understood in this document to mean its inflow area (not its "open" filter area, i.e. not the "open holes" of the porous material). In other words, when a filter F with an outer radius r of the corresponding filter tube and a height a of the filter F extends over the entire tube circumference, the area of the filter F relevant in accordance with the invention is accordingly $2\pi \cdot r \cdot a$.

The diameter D of the process space in this document means the internal diameter thereof. The distance L between the upper and lower ends of the process space in this document means the clear distance between the underside of the end B having the passages U and the surface of the rotation body described by the rotating removal device.

When the total waste liquor flow SM* which flows through the filters F of the filter tubes of the hydraulic wash column at the particular time during the supply of the stream ST* until the time $t_S$ in the course of the inventive startup of the separating process is plotted as the ordinate against the time t as the abscissa, the area under the resulting curve in the time range t=0 (commencement of supply of the stream ST*) until the time t=$t_S$, divided by $t_S$, forms the arithmetic mean, used in this document, of the total waste liquor flow SM* which flows through the filters F of the filter tubes at the particular time during the supply of the stream ST* until the time $t_s$. Where it is divided by the total area of all filters F, this gives the mean superficial velocity on the filters F.

The crystal formation temperature $T^{KB}$ of a startup liquid AT is understood in this document to mean that temperature at which the formation of acrylic acid crystals from this liquid in the course of cooling thereof sets in (this neglects the possibility of occurrence of oversaturation phenomena). Expressed in alternative terms, the crystal formation temperature $T^{KB}$ of a startup liquid AT is that temperature which is present in the startup liquid AT at the moment when, proceeding from a crystal suspension (suspension of acrylic acid crystals) obtained from the startup liquid AT by cooling it, with constant (ideally ideal) mixing, heat is supplied in order to melt the acrylic acid crystals present in the crystal suspension, and the last acrylic acid crystal has just melted (it is sometimes also referred to in the literature as dissolution temperature or as crystallization onset temperature).

Advantageously in accordance with the invention, the temperatures $T^{KB}$ and $T^S$ in the inventive startup satisfy the relationship $T^{KB} \leq T^S + 10°$ C. and particularly advantageously the relationship $T^{KB} \leq T^S + 5°$ C.

In principle, the crystal formation temperature $T^{KB}$ of the startup liquid AT may also be below the temperature of the stream ST* of acrylic acid crystals in mother liquor supplied in the course of the inventive startup of the hydraulic wash column.

In general, $T^{KB}$ in the process according to the invention will, however, not be more than 20° C., usually not more than 10° C. and often not more than 5° C. below $T^S$. Useful startup liquids AT for the process according to the invention are, for example, mother liquor removed (for example by filtration) from the suspension S, or suspension S which has been melted again after it has been obtained, or that liquid from which the suspension S has been obtained by cooling, or the melt of acrylic acid crystals purifyingly removed from a suspension S beforehand in a (the) hydraulic wash column (i.e. pure melt), or mixtures of two or more of the aforementioned possible startup liquids.

By the term "pump" this document means pumps for delivering liquids (i.e. essentially incompressible media). They have a suction side and a pressure side. Through a delivery connection connected to the suction side thereof, the delivery pump sucks in the liquid (or suspension) to be delivered. In the pump, the liquid to be delivered is brought to an elevated pressure and forced away in the desired delivery direction through a delivery connection connected to the pressure side thereof. Advantageously in application terms, the relevant delivery connections in the simplest manner are pipelines (delivery lines) through which the delivery can be effected. For the inventive procedure, especially the delivery pumps described in DE-A 10228859 and in DE 102008054587.2 are suitable (especially the radial centrifugal pumps described in these documents). For delivery of the suspension S, especially radial centrifugal pumps with a semiopen radial impeller are suitable (cf. DE 102008054587.2). The access to the suction side or pressure side of the particular pump can generally be opened or closed by means of appropriate fittings. The delivery pump P2 in particular is, advantageously in application terms, a "speed"-regulated delivery pump. In other words, the resulting delivery flow rate is established preferably via an adjustment of the speed and not via an adjustment of the free cross section in the delivery connection (not via a regulating valve), since the risk of occlusion of the delivery connection (for example as a result of crystal accumulations) is increased in the latter case.

It is additionally advantageous for the inventive procedure when, in the course of startup of the separating process, the crystal bed in the process space is formed for the first time by at first filling the melt circuit comprising the crystal melt space (crystal melt circuit) and the process space of the previously unfilled wash column with an acrylic acid-comprising startup liquid AT such that the fill height of the startup liquid AT in the process space overtops at least the filters F, preferably extends at least to the midpoint of the distance L from the lower to the upper end of the process space, more preferably extends at least to the last quarter of the distance L from the lower to the upper end of the process space, even more preferably extends at least to the upper end of the process space, even more advantageously projects beyond the process space into the distributor space and fills at least half the volume thereof, and at best projects beyond the process space into the distributor space and fills the volume thereof completely (appropriately in application terms, in the latter case, the delivery connection E2 (optionally also the delivery connection E1) and an optionally maintained control liquor circuit comprising the pump P3 and the delivery connections C1, C2 are additionally filled with the startup liquid AT).

Figure 2:
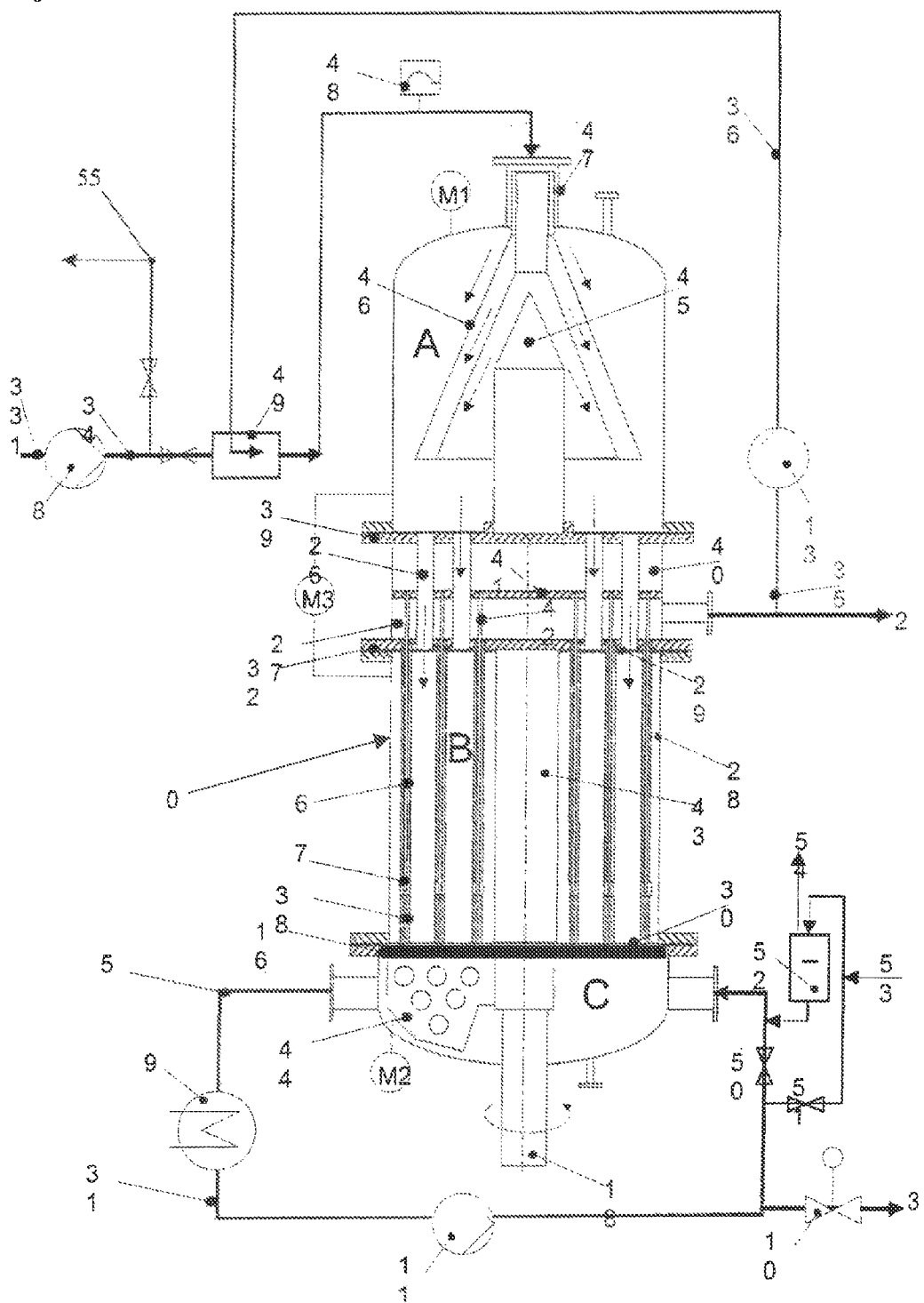
FIG. 2 is a cross-sectional view schematically showing a hydraulic wash column that has a flush liquid system.

When the hydraulic wash column has a flush liquid system, as recommended, for example, by EP-A 1448282 and shown in FIG. 2 of this document (42), the filling described is effected, preferably in accordance with the invention, via this flush liquid system.

The filling of the process space with the startup liquid AT in the process according to the invention is accompanied simultaneously by corresponding filling of the filter tubes in the manner of tubes which communicate with the process space via the filters F. As detailed in WO 2006/111565, the pressure at the filters F in the filter tube interior, during the steady-state operation of a removal process in a hydraulic wash column, is kept at a lower value than the pressure on the filters F on the process space side.

This likewise applies to the inventive startup as soon as the spaces of the hydraulic wash column have been completely filled with condensed phase and, thereafter, the supply of the stream ST* of the crystal suspension S and optionally of the control liquor stream SL* is continued (until this time, the gas phase present in the hydraulic wash column is displaced and discharged through a valve present in the top of the wash column (the valve is open until the oscillation frequency of an oscillator provided for this purpose reflects a gas phase surrounding it (the pressure difference $P_D = P_K - P_V$ at first increases constantly until the condensed phase reaches that point in the distributor space at which the pressure $P_V$ is detected; thereafter, the pressure difference $P_D$ remains essentially constant at first))).

According to detailed analysis of the processes in the course of startup of a hydraulic wash column by the applicant, the following events probably occur subsequently in the hydraulic wash column.

The liquid flow imposed as a result of the above-described pressure difference in the process space of the hydraulic wash column, first from the top downward and then, superimposed on the latter, transversely through the filters F into the filter tubes, leads, in the case of continuing supply of the stream ST* and optionally of the control liquor stream SL*, at first to acrylic acid crystals being washed up in the local environment of the particular filter F. The elevated local pressure drop which results from flow through the latter causes a compaction of this washed-up material to form snowball-like filtercakes around the filters F. Later, these filtercakes begin to grow both in terms of width and in terms of length (especially in terms of height).

When the filtercake (the compacted bed of crystals) for the first time extends in continuous form over the entire cross section of the process space, the pressure difference $P_D = P_K - P_V$ suddenly begins to decrease (channels (with comparatively high flow cross section) which still existed before and could be negotiated by liquid essentially without a significant pressure drop, through which the crystal melt space and the distributor space were able to communicate with one another in an essentially undisrupted manner, have now been eliminated by compaction). The time at which this state is attained is the time $t_S$.

It now appears to be impossible within the range of the quotient Q=L/D relevant in accordance with the invention to achieve the aforementioned continuity of the crystal bed without the crystal bed already having grown in to at least some of the passages U or having grown through the latter. When the transport of the "continuous" crystal bed is now commenced later in the startup of the separating process, at the transition to the steady operating state, filtercake can remain ("get stuck") in individual passages U. The probability of this event appears to grow with the rate of the total waste liquor flow SM* which flows out per unit total filter area in the course of startup, which is a crucial determining factor for the degree of compaction in the filtercake. However, when filtercakes remain in individual passages U, these in turn become, later in the execution of the separating process, snowballs of filtercake which grow into the distributor space.

The latter causes an above-average increase in the delivery pressure of the suspension S required to maintain the separating process, and ultimately the bursting of the protective bursting disk.

Accordingly, it is advantageous for the process according to the invention when, in the course of the inventive startup, at least over 50%, preferably over 75% or over 90% and more preferably over the entire period calculated from the commencement of supply of the stream ST* of the suspension S and optionally of the control liquor stream SL* until the time $t_S$ is reached, the total waste liquor flow SM* flowing through the filters F of the filter tubes at the particular time, divided by the total area of all filters F (this total area in this document is the sum of the areas of all filters F of the filter tubes present in the process space of the hydraulic wash column), is not more than 80, preferably not more than 75 and more preferably not more than 70 m$^3$/(m$^2$·h) or not more than 60 m$^3$/(m$^2$·h). The values of the aforementioned total waste liquor flow SM* flowing through the filters F of the filter tubes at the particular time (this is the sum of all waste liquor flows discharged into the particular filter tubes, summed over all filter tubes present in the process space of the hydraulic wash column), divided by the total area of all filters F, at least over 50%, preferably over 75% and more preferably over the entire period of supply of the stream ST* of the suspension S and optionally of the control liquor stream SL* until the time $t_s$ is reached, are advantageously in the range of >0 to 80 m$^3$/(m$^2$·h), preferably in the range of 5 to 75 m$^3$/(m$^2$·h), more preferably in the range of 15 to 65 m$^3$/(m$^2$·h) and most preferably in the range of 20 to 50 m$^3$/(m$^2$·h). It is preferred in application terms, in the course of the inventive startup (from supply of the suspension S) until the time $t_S$, to employ an essentially constant filter superficial velocity.

Appropriately in application terms, in the course of the inventive startup until the time $t_S$ (calculated from the commencement of supply of the stream ST* of the suspension S), the arithmetic mean M of the total flow of liquid supplied to the process space of the wash column (mother liquor as a constituent of the stream ST* of the suspension S and optionally control liquor in the form of the control liquor stream SL*), divided by the free cross-sectional area of the process space ($=\pi \cdot (D/2)^2$, minus, for example, the cross-sectional area of the filter tubes and the cross-sectional area of any central displacer body used in the process space) will vary in the range of >0 to 30 m$^3$/(m$^2$·h), preferably in the range of 1 to 25 m$^3$/(m$^2$·h), more preferably in the range of 5 to 25 m$^3$/(m$^2$·h) or 10 to 20 m$^3$/(m$^2$·h).

When the total flow of liquid supplied to the process space of the wash column at the particular time during the supply of the stream ST* of the suspension S until the time $t_S$ in the course of the inventive startup of the separating process is plotted as the ordinate against the time t as the abscissa, the area under the resulting curve in the time range t=0 (commencement of the supply of the stream ST*) until the time $t=t_S$, divided by $t_S$, constitutes the abovementioned arithmetic mean M.

It is advantageous in accordance with the invention when, in the course of the inventive startup, at least over 50%, preferably over 75% and more preferably over the entire period calculated from the commencement of supply of the stream ST* of the suspension S and optionally of the control liquor stream SL* until the time $t_S$ is reached, the total flow of liquid supplied to the process space of the wash column at the particular time, divided by the cross-sectional area of the process space, is >0 to 30 $m^3/(m^2 \cdot h)$, preferably 1 to 25 $m^3/(m^2 \cdot h)$, more preferably 5 to 25 $m^3/(m^2 \cdot h)$ or 10 to 20 $m^3/(m^2 \cdot h)$.

The acrylic acid content in the suspension S of acrylic acid crystals in mother liquor supplied to the process space of the hydraulic wash column via the distributor space thereof in the course of the inventive startup will frequently be $\geq 60\%$ by weight, or $\geq 70\%$ by weight, or $\geq 80\%$ by weight, or $\geq 90\%$ by weight, or $\geq 95\%$ by weight (it is naturally <100% by weight, usually $\leq 98\%$ by weight).

The process according to the invention for startup is particularly relevant when the degree of crystallization of the crystal suspension S supplied to the distributor space of the hydraulic wash column in the course of the inventive startup is $\geq 0.10$, or $\geq 0.20$, or $\geq 0.25$. In general, the aforementioned degree of crystallization in the course of the inventive startup will be $\leq 0.60$, frequently $\leq 0.50$ and in some cases $\leq 0.40$. Degrees of crystallization of the suspension S which are relevant in accordance with the invention are thus, for example, also those in the range of 0.2 to 0.3.

All statements made in this document also apply especially when the longest dimension (the longest straight line directly connecting two points on the crystal surface) of the majority (more than the numerical half of all crystals) of the crystals is 50 to 1600 μm or 200 to 900 μm.

However, they also apply especially when the acrylic acid crystals have a cubic to cuboidal appearance, while exhibiting a length to thickness ratio in the range of 1:1 to 6:1, preferably in the range of 1:1 to 4:1 and more preferably in the range of 1.5:1 to 3.5:1. The thickness of the crystals is typically in the range from 20 to 600 μm, often in the range from 50 to 300 μm. The length of the crystals is at the same time typically in the range from 50 to 1500 μm, often 200 to 800 μm.

With regard to the material properties of the hydraulic wash column for use for the process according to the invention, it is advantageous in accordance with the invention to follow the teaching of WO 03/041832. In other words, the wall material used is preferably stainless steel of DIN materials No. 1.4571, or 1.4539, or 1.4462, or 1.4541. Furthermore, the hydraulic wash column including the corresponding crystal melt circuit is preferably thermally insulated as described in US-A 2009/018347.

The mounting of the drive shaft connected in a fixed manner to the removal device follows, advantageously in accordance with the invention, the teaching of DE 102009000987.6.

A useful rotating removal device for the process according to the invention is, for example, a rotating bladed disk having passage orifices (for the crystals removed), as described, for example, in EP-A 1 448 282 and in DE 102009000987.6. The removal device can be rotated either continuously or cyclically.

Instead of a bladed disk having passage orifices, the rotating removal device may also be a single rotating removal blade (optionally incorporated into a shaft (held by a shaft)). In this case, the crystal stream removed by the rotating removal blade flows past the latter into the crystal melt space. In both cases, both in the case of the rotating bladed disk and in the case of the rotating single blade, the rotation body described by the rotating removal device (as already mentioned) separates process space and crystal melt space from one another. It will be appreciated that a useful rotating removal device is also any transition form between a circular bladed disk having passage orifices and a rotating single blade. In principle, the geometry of the bladed disk may, however, be as desired.

Since the same passages which connect the process space and the crystal melt space to one another through the removal device and/or past the removal device are available to the wash melt stream which ascends from the crystal melt space and the stream of acrylic acid crystals removed by the removal device which is conveyed into the crystal melt space (the crystals must be able to flow downward against the ascending wash melt stream), the removal device, appropriately in application terms, has an orifice ratio OV which is not too low. The orifice ratio OV is understood in this document to mean, based on the removal device in the nonrotating state, the ratio of the sum of the cross-sectional areas of the passages leading through the removal device and/or past the removal device to the cross-sectional area of the crystal bed at the end thereof facing the removal device. When the cross-sectional area of an individual passage is not constant through the passage, the smallest cross-sectional area of the passage should be used in each case to form the sum. Typically, OV is at least 0.01, or at least 0.03 or at least 0.05, frequently at least 0.1 and in many cases at least 0.5 or more (in some cases even at least 0.9). OV is naturally <1, usually $\leq 0.95$, in some cases $\leq 0.8$ or $\leq 0.5$, or even $\leq 0.2$.

As already stated, the rotatable removal device of the hydraulic wash column in the process according to the invention is advantageously configured as a bladed disk. It is preferably round or circular. As passages which connect the process space to the crystal melt space for the crystals removed from the crystal bed, it appropriately has slots (passage orifices), at the edge of which (the outline side of the slot (for example of an elongated slot) facing away from the direction of rotation)) the blades are advantageously arranged. The slots with the blades are preferably distributed over the bladed disk such that crystals are removed over the entire end of the crystal bed facing the bladed disk when the bladed disk rotates. The slots are advantageously aligned radially and each slot is equipped with an oblique blade with which the crystals are removed from the crystal bed. The distribution of the slots over the bladed disk is preferably also configured such that, in the event of a rotation of the bladed disk, essentially the same mass flow of crystals flows through each slot. The particular blade appropriately extends beyond the surface facing the crystal bed (this does not take account of any profile thereof which exists, i.e. the reference point is the highest point in the profile) (typically by 1 to 15 mm, often 2 to 10 mm, or 3 to 5 mm), such that the blade removes crystals and supplies them to the slot orifice.

The radius of bladed disks suitable in accordance with the invention for industrial scale processes may, for example, be 300 to 3000 mm. The aforementioned slots frequently have an elongated hole geometry (the definition of an elongated hole can be found, for example, in DE-A 102007028333 and in DE-A 102007028332). However, the slot geometry may also be rectangular, or between that of an elongated hole and that of a rectangle.

The hole diameter (distance between the two longitudinal edges of the elongated hole) may, for example, be 20 to 100 mm (typically 50 to 70 mm), and the distance between the two hole centers may be 100 to 500 mm. The surface of the bladed disk facing the crystal bed is, appropriately in application terms, also provided with a profile of concentric channels (the channel cross section is advantageously triangular; the channel depth may, for example, be 2 to 10 mm, or 3 to 7 mm, the channel width 10 to 15 mm, and the distance between successive channels in radial direction may be such that the corresponding triangular cross sections have common vertices). The profile ensures a very substantially homogeneous distribution of the wash melt which flows out of the wash melt space back into the process space over the cross section of the process space. FIGS. 5 and 8 of EP-A 1448282 show illustrative configurations of a bladed disk suitable in accordance with the invention as a removal device. The angle γ enclosed by the surface of the removal elements of the removal device (for example the removal blades) and the axis of rotation of the drive shaft in the process according to the invention is frequently 20° to 70° and in many cases 30° to 60°. The drive shaft in the process according to the invention projects, coming from below, in an advantageous manner in application terms, up to the bladed disk (or generally up to the removal device). Appropriately in application terms, the bladed disk is borne (supported) by lamellae (elements) which are equipped with orifices and run away radially from the drive shaft (44).

Typical crystal mass supply flows are, based on the cross-sectional area of the process space at the supply end thereof, in the process according to the invention, 1 to 20 $t/m^2 \cdot h$ (t=metric tonne). The speed of the drive shaft of the removal device is typically in the range from 2 to 40, frequently 4 to 20 and often 6 to 15 or 4 to 10 per minute. The length of the drive shaft of the removal device is, especially for industrial scale processes, 0.5 to 4 m.

The crystal melt circuit in a hydraulic wash column for a process according to the invention is, appropriately in application terms, such that it is capable of retaining a significantly larger reservoir of crystal melt than the crystal melt space alone (based on the total volume of the crystal melt circuit, generally only 30 to 60% by volume or 40 to 50% by volume is accounted for by the volume of the crystal melt space; irrespective of this, in the steady operating state, the ratio of mass flow circulated in the melt circuit to crystal flow which has been removed from the lower end of the crystal bed by the rotating removal device and conveyed into the crystal melt space is, appropriately in application terms, generally 2 to 30:1 and preferably 5 to 20:1).

In other words, the crystal melt circuit normally has a low content of as yet unmolten removed acrylic acid crystals, which firstly promotes the conveying thereof. Secondly, the absolute heat capacity of the liquid proportion of the contents of the melt circuit is significantly higher than the absolute heat capacity of the solid proportion of the melt circuit (this does not take account of heats of phase transition).

The crystal stream supplied to the crystal melt space is suspended in the crystal melt circulated therein and this suspension is subsequently conducted in the melt circuit through a heat transferer (melter) W which introduces the heat required to melt the crystals into the melt circuit by an indirect (preferred) or direct route. Owing to the aforementioned relationships between the absolute heat capacities, the input of heat into the melt circuit required to achieve the desired melt of the crystals results merely in a comparatively small temperature increase, which is advantageous for the acrylic acid which has a marked tendency to undesired free-radical polymerization owing to the associated thermal stress which is only comparatively minor.

In the ideal case, the crystal melt present in the crystal melt space has, in steady-state operation of the separating process, melting point temperature (or crystal formation temperature) of the crystals removed, based on the melt thereof (ideally=14° C.). Typically, this is exceeded in the crystal melt circuit beyond the heat transferer W by not more than 10° C., better by not more than 5° C., preferably by not more than 3 or 2° C. and more preferably by not more than 1° C.

Advantageously, in the process according to the invention, the delivery connection G1 is conducted through the heat transferer W.

Appropriately in application terms, the heat transferer W used is a tube bundle heat transferer. This is an indirect heat transferer. In other words, the heat is not transferred in direct contact, forced by mixing, between fluid heat carrier and the fluid mixture which requires the input of heat. Instead, the heat is transferred indirectly between the fluids separated by a dividing wall.

Such tube bundle heat transferers normally consist of an enclosed wide outer tube which encloses the numerous, generally smooth or ribbed, transferer tubes of small internal diameter secured in opposite tube plates.

The distance from tube center to tube center in the bundle tubes is, appropriately in application terms, 1.3 to 2.5 times the outer tube diameter. The high specific heat transfer area which arises—as the exchange area per unit space required— is a known advantage of tube bundle heat transferers as heat transferers W for the process according to the invention. In principle, the tube bundle heat transferer in the process according to the invention may be arranged vertically or horizontally. Preferably in accordance with the invention, it is arranged horizontally.

Preferably in accordance with the invention, the contents of the melt circuit flow within the transferer tubes. The fluid heat carrier (advantageously in accordance with the invention a mixture of water and glycol (for example with 10 to 60% by weight of glycol; preference is given to a mixture of 70% by weight of water and 30% by weight of glycol or 65% by weight of water and 35% by weight of glycol; its temperature is appropriately 25 to 40° C.)) flows, preferably in accordance with the invention, outside the transferer tubes. Guide plates for better conduction of the fluid heat carrier in the outer space are favorable in accordance with the invention and generally serve the additional purpose of supporting the transferer tubes. The guide plates generally increase the flow rates in the outer space and hence, inter alia, the heat transfer coefficients. According to the flow direction of the outer space fluid in relation to the transferer tubes, a distinction can be drawn, for example, between longitudinal flow and crossflow, and also transverse flow, tube bundle heat transferers. In principle, the fluid heat carrier can also be moved around the transferer tubes in a meandering manner and only viewed over the tube bundle heat transferer is it conducted in cocurrent or countercurrent to the fluid mixture which absorbs the heat.

In the single-flow tube bundle heat transferer, the stream of the melt circuit moves through all transferer tubes in the same (one) direction.

Multiflow tube bundle heat transferers comprise tube bundles divided into individual sections (the individual sections generally comprise an identical number of tubes). Dividing walls divide chambers which adjoin the tube plates (through which the transferer tubes are conducted with sealing and to which they are secured) into sections and deflect the stream which enters the chamber part from one section (and absorbs the heat transferred) into a second section and hence back. The heat-absorbing stream flows, according to the number of sections, more than once (twice, three times, four times, etc.) through the length of the tube bundle heat transferer at comparatively high speed in alternating direction (two-flow, three-flow, four-flow, etc. tube bundle heat transferer). The heat transfer coefficient and exchange distance increase correspondingly.

Alternatively to the tube bundle heat transferer, the heat transferer W used for the process according to the invention may also be a plate heat transferer (plate heat exchanger). Plate heat transferers are normally composed in the manner of filter presses generally of plates (generally of graphite or metal, for example stainless steel) which are corrugated or have some other kind of profile and are provided with channels for the fluid heat carrier and the fluid mixture which absorbs the heat transferred, in a compact design. The two heat-exchanging fluids then flow in cocurrent, countercurrent and/or crosscurrent as alternating thin layers (for example upward and downward) through the chamber rows thereof and are in heat transfer with one another at both chamber walls. The corrugated plate profiles increase the turbulence and improve the heat transfer coefficients. Plate heat exchangers usable for the inventive purpose are described, for example, in EP-A 1079194, U.S. Pat. No. 6,382,313, EP-A 1232004 and WO 01/32301. It will be appreciated that the heat transferers W used may also be spiral tube heat transferers or other heat transferers.

Advantageously, the heat transferer W used for the process according to the invention is a three-flow tube bundle heat transferer, through whose tubes the substance mixture of the melt circuit is forcibly conveyed.

The outer tube diameters may, with a wall thickness of 2 mm of the tubes, be 25 mm. In the case of a length of the tubes of 3000 mm, the total number thereof is, appropriately in application terms, 121 or 225 (in each case approx. one third of the total number of tubes for one flow direction). The tube pitch is simultaneously advantageously 32 mm (60° pitch). 9 or 20 deflecting plates mounted between the tube plates (in which the exchanger tubes are secured) (deflecting plate thickness: in each case 5 mm) divide the cylindrical space (the primary space) surrounding the heat transferer tubes into 10 or 21 longitudinal sections (segments). All deflecting plates are circular in principle. The circle diameter is 584 or 492 mm. In each of the circular deflecting plates, however, a circular section has been cut away, the radial depth of which from the circumference line inward is 82 or 94 mm, so as to give rise to a corresponding passage for the water-glycol mixture as the heat carrier, these passages being successively opposite one another in alternation (otherwise, the deflecting plates are secured with sealing to the vessel wall; where the heat transferer tubes meet the deflecting plates there are corresponding bores in the deflecting plates). The inlet of the heat carrier and of the substance mixture which absorbs the heat may, appropriately in application terms, be on the same side of the heat transferer. The mass flow of the heat transferer supplied is typically 20 000 to 80 000 kg/h with simultaneously supplied melt circuit flows of 50 000 to 200 000 kg/h. In the case of a configuration as in FIG. 2, the working pressure (without taking account of hydrostatic effects) on the suction side of the pump P1 (immediately after exit of the melt circuit from the heat transferer W) in the process according to the invention is below the pressure in the crystal melt space (C) and is frequently 0.1 to 4 bar. The working pressure on the pressure side of the pump P1 (indirectly after exit of the melt circuit from the pump P1) is, in the case of a configuration according to FIG. 2 in the process according to the invention, frequently 1 to 10 bar.

The material of manufacture of the tube bundle heat transferer is preferably stainless steel of the DIN 1.4571 type, or 1.4541, or 1.4306 on the tube side, and carbon steels such as 1.0425 or stainless steels such as 1.4541, or 1.4571, or 1.4306 on the outer side.

Advantageously in accordance with the invention, the suspension S of acrylic acid crystals for the process according to the invention is prepared as described in DE-A 10 2007 043748 and in DE-A 10 2007 043758, by cooling suspension crystallization in an indirect heat transferer.

From the heat transferer, the suspension of acrylic acid crystals in mother liquor obtained therein is, advantageously in application terms, conducted first into a mixed buffer tank PT, as described in DE-A 10 2007 043759. From this buffer vessel (as the source QS), the crystal suspension can then be sucked in by the delivery pump P2 as suspension S (via the delivery connection E1 which connects the buffer tank PT to the suction side of the delivery pump P2).

In general, the temperature of the suspension S of acrylic acid crystals supplied to the distributor space of the hydraulic wash column in the process according to the invention is in the temperature range from −25° C. to +14° C., frequently in the range from −5° C. to +12° C. and preferably in the range from +4 or from +6 to +9° C.

The content of acrylic acid in the mother liquor present in the suspension S will generally still be ≧70% by weight. It may, however, also be ≧80% by weight, or ≧85% by weight, or ≧87% by weight, or ≧90% by weight, or ≧92% by weight, or ≧94% by weight, or ≧95% by weight, or ≧96% by weight, or ≧97% by weight, or ≧98% by weight, or ≧99% by weight.

Even before commencement in the process according to the invention of supply of a stream ST* of the suspension S from the buffer tank PT as the source QS to the distributor space of the hydraulic wash column, it is advantageous in accordance with the invention to put the delivery pump P2 into operation, and to suck in the suspension S via the delivery connection E1 which connects the suction side of the delivery pump P2 to the buffer tank PT. Subsequently, the suspension S sucked in is forced by the delivery pump P2 into the delivery connection E2 which leads from the pressure side of the delivery pump P2 into the distributor space of the hydraulic wash column. In flow direction, on the route from the pressure side of the delivery pump P2 to the inlet (inlet stub) of the distributor space of the hydraulic wash column, upstream of the inlet into the distributor space in the delivery connection E2, however, it is advantageous in accordance with the invention for a first fitting to be incorporated, which at first blocks the delivery connection E2.

In addition, between the pressure side of the delivery pump P2 and the first fitting of the second delivery connection E2, advantageously in accordance with the invention, a delivery connection E3 ((55) in FIG. 2) which leads back into the buffer tank PT branches off, the connection of which to the buffer tank PT can be blocked by a second fitting which is, advantageously in accordance with the invention, incorporated into the delivery connection E3, but is at first kept open. As a result, the suspension S, by virtue of the delivery pump P2 already in operation, at first circulates in a simple manner through the delivery connections E1, E2 and E3 via the buffer tank PT. From the time from which the stream ST* of the suspension S is to be supplied to the distributor space of the hydraulic wash column in the context of the inventive startup, the second fitting blocks the delivery connection E3 to the buffer tank PT and the first fitting simultaneously opens the delivery connection E2 to the distributor space of the hydraulic wash column (such fittings used may, for example, be valves, flaps or ballcocks for closing and opening). Both the mixing in the buffer tank PT and the conveying of the crystal suspension S in the process according to the invention are advantageously effected so as to result in a minimum level of fragments and/or any other change in shape of the suspended crystals. This applies especially to the above-described circulation of the crystal suspension S.

In the case that, in the course of the inventive startup, prior to the supply of the stream ST* of the suspension S via the distributor space and through the passages U into the process space of the hydraulic wash column, the melt circuit comprising the crystal melt space, and also the process space and the distributor space, and also the delivery lines E2 (and optionally E1), C1, C2 and the delivery pump P3, are completely filled with the acrylic acid-comprising startup liquid AT, and, with the supply of the stream ST* of the suspension S into the distributor space, accompanying this supply, control liquor stream is also conducted simultaneously into the distributor space and/or directly into the process space, it is appropriate in application terms already to put the delivery pump P3 into operation prior to the commencement of supply of the stream ST* of the suspension S into the distributor space, and to allow a stream of the startup liquid AT to circulate through the circuit formed from distributor space, process space, filter tube interior, delivery connection C1, delivery pump P3 and delivery connection C2.

When, in the process according to the invention for startup, a control liquor stream SL* is also used, this is a recycled substream of the total waste liquor flow SM* conducted out of the wash column via the filter tubes. Normally, the aforementioned recycling of the waste liquor substream is effected with essentially the same temperature with which the waste liquor stream SM* is conducted out of the wash column. This temperature typically corresponds to that temperature with which the suspension S of the acrylic acid crystals in mother liquor is supplied to the distributor space of the hydraulic wash column. Of course, the aforementioned recycling of the waste liquor substream as control liquor substream SL* can also be effected, for example, via a direct and/or indirect heat exchanger which increases the temperature of the waste liquor substream recycled as the control liquor stream SL*. Appropriately in application terms, the temperature of the control liquor stream SL* should, however, be not more than 15° C., preferably not more than 10° C. and more preferably not more than 5° C. above the temperature of the stream ST* of the suspension S conducted into the distributor space of the hydraulic wash column. The aforementioned also applies correspondingly to the steady-state operation of the removal process in the hydraulic wash column.

An additionally used control liquor stream pursues, both in the course of the inventive startup and in steady-state operation, the purpose of influencing the hydraulic pressure drop and hence the resulting force acting on the crystals, the crystal bed (for example the advancing force acting on the continuous crystal bed). When the mother liquor flow supplied, accompanying the supply of the suspension S of the acrylic acid crystals in another liquor, is inadequate in this regard, or it fluctuates during the supply period to a certain degree with time, this can be compensated for by means of the control liquor stream (a detailed explanation of the mode of action of the control liquor stream can be found in WO 2006/111565). The control liquor stream can be supplied to the process space of the hydraulic wash column either via the distributor space and through the passages U, or by a direct route into the process space. In principle, it is possible to conduct control liquor into the process space at different heights in the crystal bed. Normally, control liquor is, however, always supplied above the filters F.

Since the position of the buildup or filtration front in steady-state operation of the hydraulic wash column is influenced by factors including the rate of advance of the crystal bed in the wash column, the position of the buildup front, in the event of occurrence of disruption, can be held stable ("controlled") by adjusting the control liquor flow (cf. WO 2006/111565). An increasing (decreasing) flow rate of the control liquor stream generally brings about a downward (upward) shift of the buildup front. Alternatively, the flow rate of the suspension stream ST* supplied would have to be varied. For the reasons detailed in WO 2006/111565, the buildup front in the hydraulic wash column should be positioned neither too high nor too low. The portion of the crystal bed which, in steady-state operation, commences at the crystal removal and extends up to the start of the filter F is also referred to as the wash zone. The part of the crystal bed above it, which extends up to the buildup front, is also known as concentration zone. This is followed up to the upper end of the process space by what is known as the suspension zone. Typically, the filter tubes of the hydraulic wash column extend into the wash zone, but are no longer hollow in this region of the wash column (cf., for example, WO 01/77056, WO 03/41833 and WO 03/41832). This part of the filter tubes is also referred to as the filter tube displacer.

The rate of the control liquor flow can be regulated, for example, by adjusting the speed of the delivery pump P3 and/or by means of an additional regulating valve.

In principle, the supply of the suspension S and the supply of control liquor stream into the distributor space of the hydraulic wash column can be effected in a spatially separate manner. Of course, the feed stream of the suspension S and a control liquor stream supplied to the distributor space may, however, also already be combined outside the distributor space and mixed with one another, and the resulting mixed stream (effectively via a combined delivery connection E2/C2) can be conducted into the distributor space of the hydraulic wash column.

For example, the two streams can be mixed by conducting the two delivery connections E2 and C2 first into a static mixer and, downstream thereof, run to the distributor space of the hydraulic wash column now as only one common delivery connection.

Alternatively, the delivery connections E2 and C2 upstream of the supply space of the hydraulic wash column may be designed as coaxial delivery lines (pipelines). Appropriately in application terms, the suspension S is conducted within the inner delivery connection (in the inner pipeline) and the control liquor in the outer delivery connection (in the outer pipeline). A mixing zone of, for example, 0.5 to 20 m upstream of entry into the distributor space of the hydraulic wash column ends the inner tube, and only the outer of the two tubes is continued as what is then a common delivery connection E2, C2 to the distributor space. Advantageously in accordance with the invention, the inner pipeline narrows toward its end (generally conically; for example from internal diameter approx. 80 mm to internal diameter approx. 50 mm). In this way, the inner pipeline which ends functions as a motive nozzle (cf. pages 3/4 of DE-A 102006045089) with the suspension S as the motive jet. As such, it sucks in some of the control liquor flowing on the outside immediately beyond the end of the inner pipeline in flow direction and mixes therewith to form the mixed stream which flows as such into the distributor space. The internal diameter of the outer pipeline may, with the given dimensions of the inner pipeline, be 150 mm, for example. The distance from the inside of the wall of the outer pipeline to the outer wall of the inner pipeline may, for example, be 40 to 50 mm (e.g. 46 mm). The rate of the control liquor flow conducted on the outside may be 5 to 80 m³/h, and the rate of the suspension flow conducted on the inside 10 to 50 m³/h.

The pressures $P_K$ and $P_V$ can be determined, for example, like the pressure measurements of WO 2006/111565. Advantageously in accordance with the invention, membrane manometers mounted outside the hydraulic wash column are used for this purpose. The transducers are connected to the column interior via small open bores (typical bore hole diameter=0.1 to 3 mm) which end in a stub leading to the membrane manometer (in principle, the procedure is analogous to the remarks in DE-A 10211290 and in WO 2006/111565). In order to prevent the aforementioned bores and stubs from becoming blocked by crystals, they and the manometers are, advantageously in accordance with the invention, trace-heated with a small heat flow (in general, housing of the hydraulic wash column in a heated building is sufficient for this purpose, as described, for example, in WO 03/041832 and US-A 2009/018347). Of course, the pressure difference $P_D$ can also be detected directly via a pressure difference measurement, as likewise described in WO 2006/111565. Preferably in accordance with the invention, the manometers M1 and M2 used (cf. FIG. 1 and FIG. 2) are those of the 2088 GS membrane sensor type, measurement range: 0-10 bar, from the supplier Rosemount. Suitable pressure difference manometers M3 (cf. FIG. 2) for the process according to the invention are preferably those of the 3051 CD difference membrane sensor type, measurement range: 0-500 mbar, from the supplier Rosemount.

Advantageously, the particular bore concludes flush on the inside of the particular space of the hydraulic wash column. The diameter of such open bores is, viewed from the column interior, appropriately in application terms, $\leq 5$ mm, often $\leq 3$ mm and generally $\geq 0.1$ mm. It is appropriate in application terms to employ a bore diameter which narrows continuously or in stages toward the column interior through the wall.

Until the time $t_S$ is reached in the course of the inventive startup, the heat exchanger W, the delivery pump P1 (at least from commencement of the supply of the suspension stream ST*) and the rotatable removal device are, preferably in accordance with the invention, out of operation and the flow through the outlet A is preferably blocked.

In principle, the aforementioned elements may, however, also already be put into operation to a limited degree. When the flow through the outlet A is already open to a limited degree prior to the time $t_S$, this should be taken into account correspondingly in the flow rate of the stream ST* and optionally SL* in the course of operation of the inventive filling. In addition, the rotational movement of the removal device should not be too strong, since this has an adverse effect on the process of concluding the crystal bed and the further buildup thereof. The heating output of the heat exchanger W may already be different than zero prior to the time $t_S$ in order to melt acrylic acid crystals which already get into the melt circuit in the course of filling with suspension S. It should, however, appropriately in application terms, not be higher than 50% of the heating output employed in steady-state operation of the separating process prior to the time $t_s$ (for example, it could be 10% or 20% of this heating output). Heating output is understood to mean the heat flow released to the melt circuit. It can be adjusted as required by appropriate variation of the temperature of the heat carrier (this normally varies, as already mentioned, in the range of 25 to 40° C.) and/or variation of the flow rate thereof.

When the time $t_S$ has been reached in the course of the inventive startup, (as already stated, advantageously with the removal device not rotating at first and with the melt circuit out of operation) the supply of the stream ST* of the suspension S into the distributor space and the supply of any control liquor stream SL* additionally used are interrupted. Thereafter, the melt circuit and the rotation of the removal device are put into operation, the sequence of startup of the individual elements thereof being essentially as desired. However, the sequence is preferably as described below.

Advantageously in accordance with the invention, the heating output of the heat exchanger W (based on a delivery pump P1 in operation) is at first set to about 50 to 80% of the heating output thereof in steady-state operation. Thereafter, the delivery pump P1 and then the rotation of the removal device are put into operation (both are set to the operating value thereof in the steady state).

From the time from which the rotation of the removal device has been put into operation, the supply of the suspension S from the source QS through the delivery connections E1, E2 via the distributor space and through the passages U into the process space of the wash column is restarted. The same applies to any control liquor stream additionally used. The sequence of startup is unimportant.

The flow rates are selected such that the crystal bed and the level thereof (buildup front) begin to move downward. The flow rates of suspension stream and optionally control liquor stream required for this purpose need not necessarily be greater than those which have been employed in the course of the inventive startup until the time $t_S$ (preferably in accordance with the invention, essentially constant flows and flow rates are employed over time until the time $t_S$). In principle, it is possible in some cases, even in the case of otherwise constant flows, for lower flow rates than before the time $t_S$ to be sufficient to achieve commencement of downward movement not only of the crystal bed but also of the level thereof (the buildup front thereof). This is because, in the course of the inventive startup until the time $t_s$, the result is increasing compaction of the crystal bed which forms.

A resulting consequence even in the case of maintenance of the rate of waste liquor flow, is a hydraulic pressure drop which increases over the operating time, which, in the case of restart after passing the time $t_S$, may be sufficient to set the crystal bed and level thereof in motion.

In less favorable cases, however, a waste liquor flow based on the unit of the total area of all filters F of up to 250 m³/(m²·h), or of up to 320 m³/(m²·h), may be required in order to set the crystal bed and the level thereof (buildup front) in motion. Higher values are generally not required.

In particularly favorable cases, a waste liquor flow on a corresponding basis of only 40 m³/(m²·h) may also already be sufficient in order to set the crystal bed and the level thereof in motion. The level of the crystal bed in the process space (the "buildup front") begins to fall.

Since acrylic acid crystals are now already being removed by the removal device at the lower end of the crystal bed, and being conveyed into the crystal melt space and melted in the melt circuit, it is now appropriate in application terms to put into operation the inhibition of polymerization (metered addition of polymerization inhibitor and optionally air or another oxygen-comprising gas) in the melt circuit.

It will be appreciated that the process according to the invention, for reasons of safety, must be performed in the presence of polymerization inhibitors in order to rule out undesired free-radical polymerization of acrylic acid.

While the mother liquor of the suspension S normally comprises polymerization inhibitors such as phenothiazine (PTZ) and/or the monomethyl ether of hydroquinone (MEHQ) in enriched amounts, caused by the suspension crystallization employed for the generation thereof, the acrylic acid crystals suspended in the suspension S are normally depleted in polymerization inhibitors, since they are not usually incorporated in the crystal which forms in the course of crystal formation.

When such crystals removed from the crystal bed are melted in the melt circuit, this leads, where this melting takes place at discrete points, to local underinhibition of the melt which forms. Such underinhibition harbors an increased risk of an undesired free-radical polymerization of the acrylic acid which self-accelerates as a result of the heat of polymerization released, and this risk therefore has to be counteracted.

Such counteraction is possible in a comparatively simple manner by metering a solution of the appropriate inhibitor (with comparatively increased inhibitor concentration) in pure product (in a melt of acrylic acid crystals purifyingly removed beforehand) into the melt circuit in flow direction beyond the heat transferer W (if it is integrated into the delivery connection G1) but upstream of the suction side of the delivery pump P1 (metered addition beyond the pressure side of the delivery pump P1 would cause an increased feed pressure, but is possible in principle).

Advantageously in accordance with the invention, this inhibitor solution can be metered in with that temperature (for example via a T-piece) that the melt circuit has at the feed point. Frequently, the inhibitor solution is, however, metered in with a temperature in the range from 15 to 35° C. Typical inhibitor contents of such an inhibitor solution supplied are, for example, 0.1 to 1.5% by weight of PTZ and/or 0.1 to 5% by weight of MEHQ. Based on the mass flow rate in the outlet A, the mass flow rate of the inhibitor solution metered into the melt circuit is generally 0.1 to 10%, preferably 0.5 to 3%. When inhibition is effected with PTZ, the proportion by weight thereof in the crystal melt space and in the outlet A is typically 50 to 500 ppm by weight. When inhibition is effected with MEHQ, the proportion by weight thereof in the crystal melt space is typically 10 to 500 ppm by weight. Especially when the melt circuit is polymerization-inhibited by means of MEHQ (the type of polymerization inhibition is oriented primarily to the contemplated use of the pure product withdrawn from the outlet A; when it is intended to use the discharged pure product primarily in polymerization reactions, the inhibition is effected preferably with the "MEHQ storage inhibitor"; when it is intended to use the discharged pure product primarily for chemical processes other than polymerization reactions, preference is given to inhibiting with the process inhibitor PTZ (in particular when the chemical process is subject to thermal stresses)), there is additional coinhibition by introduction (for example nozzle injection) of a molecular oxygen-comprising gas into the melt circuit. Useful such molecular oxygen-comprising gases include in particular mixtures of molecular oxygen and inert gas (e.g. $N_2$, $CO_2$, He, Ar) (the molecular oxygen-comprising gas is preferably free of water vapor (dried beforehand) and free of solid particles (filtered beforehand)). It will be appreciated that it is also possible to meter in pure molecular oxygen. Preferably in accordance with the invention, the molecular oxygen-comprising gas metered in is air.

Advantageously in accordance with the invention, the molecular oxygen-comprising gas is metered into the melt circuit in flow direction thereof on the pressure side of the delivery pump P1 downstream of the outlet A.

For the purpose of metered addition of the molecular oxygen-comprising gas into the melt circuit, the crystal melt stream forced away by the delivery pump P1 is divided with the aid of a T-piece into two substreams of identical composition. The ratio of the flow rates thereof is appropriately adjusted by means of two fittings (50) and (51). The closure of this division which previously existed has now been removed. The smaller of the two substreams (it is generally at least 5%, but normally not more than 20%, of the overall stream present prior to the division; the other substream is referred to as the main substream) then flows through an oxygen introduction zone (for example, as the motive jet, a jet nozzle (cf. DE-A 102006045089) in which the molecular oxygen-comprising gas (preferably air) is sucked in). In the simplest case, a T-piece at the start of the introduction zone is used to feed in the molecular oxygen-comprising gas from a pressure conduit (53). The molecular oxygen-comprising gas preferably has that temperature that the melt circuit also has at the feed point. However, it is in many cases at ambient temperature ($\geq 15°$ C. and $\leq 35°$ C.).

Downstream of a sufficiently long mixing zone, the substream with the molecular oxygen-comprising gas stream metered in is conducted through a gas separator (52) in order to remove gas undissolved therein again. This measure pursues the purpose of preventing such undissolved gas from collecting later in the process in the form of a gas bubble below the lower end of the crystal bed, and hence reducing the rise of the wash melt out of the crystal melt space into the crystal bed and hence ultimately the washing effect of the hydraulic wash column.

In principle, such a gas separator used may be any known type of gas separator, as also detailed, for example, in EP-A 492400. These include centrifugal separators (for example cyclone separators), and likewise gravitational separators. The latter are preferred in accordance with the invention owing to their simple design with simultaneously satisfactory separating action. Ultimately, a vessel equipped with baffle plates is sufficient in this regard. In the simplest embodiment, the aforementioned substream is conducted into the middle of the vessel onto baffle plates mounted there. At the upper end of the vessel is the outlet for the lower-density gas (54) separated out in the baffle region, and in the lower region of the vessel is the outlet for the higher-density liquid phase.

Beyond the gas separator, the substream enriched with molecular oxygen and the main substream are combined again to give an overall stream.

After the startup of the inhibition of polymerization, the flow rate of the control liquor stream which is preferably used additionally in accordance with the invention is advantageously reduced at first, in order that the level of the crystal bed does not decline further but is established at a desired height. Then, appropriately in accordance with the invention, the flow through the outlet A is opened. For this purpose, a valve or another fitting is normally mounted at the outlet.

The passage is opened merely to such an extent that a sufficient liquid flow still ascends from the crystal melt space into the crystal bed moving toward the removal device.

The flow through the outlet A is preferably at first restricted to such an extent that the liquid ascending out of the crystal melt space ascends up to the filters F and is conducted out of the process space as a constituent of the waste liquor stream through the filters F and the filter tubes (less advantageously, the height of rise could be regulated by corresponding closed-loop control of the flow through the outlet A even from the start, at a level below the lower edge of the filters F).

The temperature regulation of the crystal melt circuit is now preferably put into operation, and the heating output of the heat transferer W is regulated such that the temperature in the crystal melt circuit beyond the heat transferer W is not more than 10 or 5° C., preferably not more than 3 or 2° C. and more preferably not more than 1° C. (but typically ≧0.01° C.) above the crystal formation temperature of pure crystals removed from the crystal melt thereof (14° C.) (at the start, the regulation can still be effected by hand, before being transferred to the automatic regulation system; the latter is implemented with the aid of appropriate thermocouples or resistance thermometers).

Finally, appropriately in application terms, continuously or at particular time intervals, the flow through the outlet A is opened to an increasing degree until the crystal bed temperature which has been selected as the control parameter and is between 14° C. and the temperature of the crystal suspension supplied to the distributor space (the target temperature) is present at the crystal bed height contemplated for the desired position of the wash front in the crystal bed below the filters F. For example, the control parameter (target temperature) selected may be the arithmetic mean of the two temperatures (cf. DE-A 10036881 and WO 02/09839). From this time, the passage of the outlet A can be regulated automatically with the aid of the deviation of the temperature measured at the crystal bed height envisaged for the wash front position from the aforementioned target temperature. When the temperature measured at the crystal bed height envisaged for the wash front position is lower than the target temperature selected, the flow through the outlet A is reduced. When the temperature measured at the crystal bed height envisaged for the wash front position is higher than the target temperature selected, the flow through the outlet A is increased (for example by opening the appropriate control valve).

For example by regulating the flow rate of the control liquor stream preferably used additionally in accordance with the invention, by detecting the level of the crystal bed (of the buildup front) by measurement according to the teaching of WO 2006/111565, the filtration front can be kept at the desired height in a comparatively simple manner.

Later in the execution of the separating process, it is beneficial in application terms to automatically regulate the metering mass flow of the inhibitor solution in pure product in relation to the pure product mass flow conducted out of the outlet A (in the case of the molecular oxygen-comprising gas, the excess metered addition with subsequent removal of excess is maintained).

Sampling of the stream conducted out of the outlet A and analyzing the samples appropriately determines the time from which the discharged stream has the desired purity. From this time on, the outlet stream can be conducted, for example, into a pure product storage tank. Streams discharged beforehand with still insufficient purity can be recycled, for example for the purpose of recrystallization thereof, into the crystallization process to generate the suspension S. Alternatively, they can also be recycled into the generation of the stream from which the suspension S results by suspension crystallization (for example into the fractional condensation of the product gas mixture of a heterogeneously catalyzed partial gas phase oxidation of propane and/or propylene performed to prepare acrylic acid, as described, for example, in WO 01/77056 and in WO 08/090190 for the mother liquor removed in the hydraulic wash column.

The separating process has now moved to its steady operating state.

The number of filter tubes in a hydraulic wash column, in the case of industrial scale application of the process according to the invention, may be 3 to 200 or more. Based on the unit of the cross-sectional area of the process space of the hydraulic wash column, the number thereof is typically 10 to 100 per m². The length of the wash zone is typically 0.5 to 20 times, preferably 1 to 8 times and most preferably 2 to 5 times the distance of the filter tube closest to the outer wall of the process space from the shell (this distance is generally 25 to 500 mm, frequently 40 to 250 mm, often 80 to 200 mm).

Typical internal diameters of the filter tubes in the process according to the invention are 5 to 200 mm, frequently 10 to 100 mm, in many cases 20 to 80 mm. The wall thickness of the filter tubes is regularly 1 to 10 mm. As already mentioned, the filter tubes are, appropriately in application terms, provided at a defined height with a filter F which generally extends around the entire circumference of a filter tube. The height of the filter elements F is frequently 20 to 200 mm. The perforation thereof, which causes the filtering action of the filter element F, may either comprise holes or longitudinal slots. The slot width or the hole diameter is preferably 50 to 400 µm, for example 100 to 300 µm, in the process according to the invention. External and internal diameters of a filter tube are, preferably in accordance with the invention, constant over the length thereof. Advantageously in accordance with the invention, the filter tubes of a hydraulic wash column suitable in accordance with the invention have a uniform shape. The filter element F of a filter tube is normally adjoined in the downward direction, as already stated, by a filter tube displacer (38). No liquid is capable of penetrating into it. It may be cylindrical, conical or be configured as a combination of these forms. The outer connection diameter is generally identical to the outer diameter of the filter element. Preferably in accordance with the invention, the filter tube displacer consists of a material with a low thermal conductivity (for example Teflon or polyethylene). The length of the filter tube displacers is regularly 50 or 100 to 500 mm.

The length of the wash zone in the process according to the invention is generally 50 to 500 mm. The total height of the compacted crystal bed (of the compacted filtercake) in a hydraulic wash column in the process according to the invention is typically 300 to 4000 mm, frequently 400 to 3000 mm, in many cases 500 to 2000 mm, or 600 to 1500 mm or to 1000 mm.

The motive pressure (reported as gage pressure relative to atmospheric) in a hydraulic wash column is frequently up to 10 bar, in many cases up to 8 bar and often 1 to 5 bar or 0.5 to 4 bar. The hydraulic flow pressure drop of the mother liquor of the suspension S supplied is generally ≧100 mbar to ≦5 bar or ≦10 bar. With regard to the distribution of the filter tubes of a hydraulic wash column over the cross section thereof, it is advantageous in accordance with the invention to proceed as recommended in EP-A 1 448 282. The length of the filter tubes (not including the filter tube displacers) corresponds to the length L of the process space minus the above-specified length for the wash zone.

As a result of the freezing point depression brought about by the impurities, the temperature of the suspension S supplied to the distributor space of the hydraulic wash column is necessarily lower than the crystal formation temperature of the pure product discharged from the outlet A (of the wash melt). In the region of the wash front, there is therefore an equalization of temperature of the cold crystals originating from the cold suspension S with the wash melt, in the course of which the wash melt is partly or completely recrystallized (this recrystallization constitutes a further purification mechanism). As a result, at least some of the wash melt is recovered. The described recrystallization of the wash melt contributes to stabilization and development of the wash front, and the further the temperature of the suspension S is below the crystal formation temperature of the wash melt the more marked it is. In principle, the aforementioned temperature difference, which can be influenced by factors including the selected degree of crystallization of the suspension S, may be 15° C. and more. In many cases, a temperature difference of 4 to 10° C. and, in the case of a low impurity content of the mother liquor, often even only of 2 to 4° C., is established. When quantitative recrystallization is possible (the wash front is below the lower edge of the filters F), 100% of the crystal stream supplied to the process space can be removed ultimately from the crystal melt circuit as pure product stream (both streams have essentially the same mass flow rate; no wash melt is lost). When the difference between the temperature of the suspension S and that of the wash melt becomes too great, this can result in occlusion of the pores in the compacted crystal bed, which is deleterious to performance of the removal process as intended.

A position of the wash front at the filters F is normally associated with nonquantitative recrystallization of the ascending wash melt stream. A substream thereof is accordingly removed as a constituent of the waste liquor stream.

When the total waste liquor flow SM* which flows through the filters F of the filter tubes at the particular time during the supply of the stream ST* until the time $t_S$ in the course of the inventive startup, divided by the total area of all filters F, is predominantly at particularly low values (e.g. <20 m³/(m²·h)), there is an increasing possibility that, on startup of the crystal melt circuit beyond the time $t_S$, the wash melt stream will rise up to the filters F in an unwanted manner. A recrystallization which sets in therein may be capable of blocking the filter orifices and necessitate the use of a flush liquid recommended in EP-A 1 448 282 (typical flush acid flows (e.g. slightly heated mother liquor streams) per filter F are 10 to 1000 l/h, preferably 50 to 200 l/h). Waste liquor flows normalized to the total area of the filters F of $\geq 20$ m³/(m²·h) are therefore preferred in the inventive startup.

For the performance of the process according to the invention, it is also advantageous to slightly increase the cross section of the hydraulic wash column just upstream of (viewed from above) the rotating removal device (by 5 to 100 mm based on the diameter thereof). This enables selection of the radial extent of the removal device at a somewhat greater level than the radial extent of the crystal bed (though the former may in principle also be smaller than the latter), which promotes the homogeneous removal of crystals over the entire crystal bed cross section. To improve the suspension of the crystals removed by the rotating removal device in the crystal melt present in the crystal melt space, it is helpful to secure paddles to the drive shaft for the removal device, below the latter, which mix the crystal melt space. This purpose can also be served by reinforcing elements (for example reinforcing fins or lamellae, which generally have passage orifices), which are configured with a large area between the hub used to secure the removal device to the shaft and the removal device, and baffles secured to the inner wall of the crystal melt space (cf. for both elements, FIG. 2 of EP-A 1 448 282).

The passages U of the at least one end B in the process according to the invention pursue the purpose of a very substantially homogeneous supply of suspension S out of the distributor space into the process space over the cross section of the process space. Advantageously in accordance with the invention, the passages U are distributed homogeneously over the end B. The passages U preferably have circular orifices and a cross section which is preferably constant along the passage U.

The orifices of the passages U advantageously have cross-sectional areas which, based on a circular shape, correspond to a diameter of 15 to 300 and preferably of 50 to 150 mm.

The height (length) of the passages U in the process according to the invention may be up to 1000 mm (in each case measured from the distributor space to the process space). In general it is at least 50 to 200 mm. It is frequently 400 to 800 mm. The ratio of the total area of all orifices of the passages U facing the process space to the total area of the process space cross section in the process according to the invention is frequently 0.10 to 0.60 and in many cases 0.20 to 0.40.

In addition to the end B having passages U, the distributor space, according to the recommendation of EP-A 1 448 282, may comprise distributor space aids which are beneficial for very substantially homogeneous supply of suspension S (viewed over the cross section of the process space) out of the distributor space into the process space. Useful such distributor space aids are, for example, packings accommodated in the distributor space. However, such a distributor space aid may also be a stirrer which stirs the contents of the distributor space and keeps it very substantially homogeneous as a result. Further possible distributor space aids are, for example, a distributor space cone according to FIG. 2 of EP-A 1 448 282 or guide plates according to FIG. 7 of EP-A 1 448 282. However, useful distributor space aids are also "funnels" nested one inside another, as shown in FIG. 2 of this document (46). The funnel necks each project into the feed stub of the distributor space, and the funnel heads project into the distributor space. Between the spaced surfaces of the funnel heads, the suspension S approaches the cross section of the distributor space distributed homogeneously over the latter. The positioning of a displacer body (43) in the center of the process space of the hydraulic wash column, as recommended in EP-A 1 448 282, is likewise advantageous for homogenization of the crystal bed development. The central displacer body normally has a circular cylindrical shape, the outer diameter of which is typically greater than that of a filter tube. In principle, however, it is also possible for the centrally positioned displacer body, at the height of the filters F of the filter tubes, to have a filter of height corresponding to the filters F and be configured with a hollow interior, as a result of which it assumes the effect of a larger filter tube. In this case, the displacer body should be considered and taken into account like a filter tube for the purposes of the present invention. Hydraulic wash columns which are particularly suitable for the process according to the invention are thus especially those which follow the details of EP-A 1 448 282 and of DE 102009000987.6. One embodiment of such a hydraulic wash column is shown in FIG. 2 of this document.

Advantageously in accordance with the invention, in the hydraulic wash column (0) according to FIG. 2, the distributor space (A) is separated from the process space (B) by an end B (32) and by a further end B* (39), which in turn define a cylindrical space. Both ends have orifices (preferably circular bores (holes)), the orifices of the end B* (39) being connected to some (the second group) of the orifices of the end B (32) via continuous connection pieces, the passages U (26) (both orifices open into a passage U (26)). Through the passages U (26), the suspension S to be separated passes into the process space (B) of the wash column (0).

The end B (32) additionally has a first group of orifices which do not have a counterpart in the end B* (39) and which open into the filter tubes (6). This second group of orifices are preferably circular bores (holes).

Figure 3:
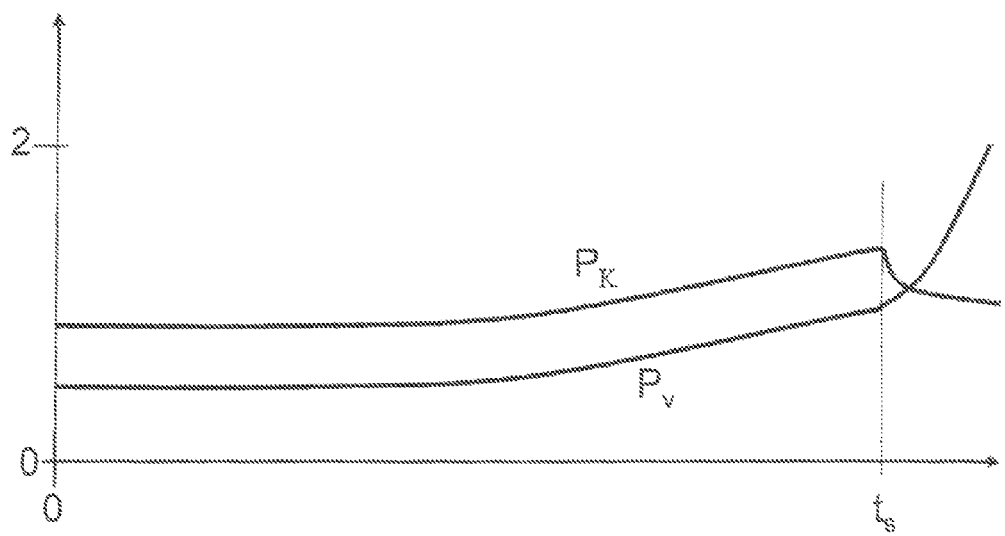
FIG. 3 shows the profile of the pressures of $P_K$, $P_V$, and the pressure difference $P_D$ until the time $t_s$ is passed.
Figure 3:
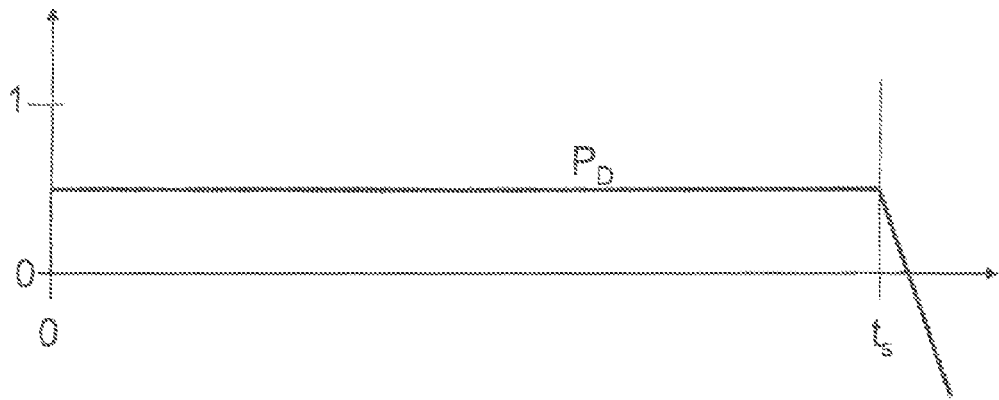

This first group of orifices is, just like the filter tubes (6) which open into these orifices, preferably distributed homogeneously over the cross section of the end B (32), as shown, for example, in FIG. 3 of EP-A 1 448 282.

This homogeneous distribution defines predominantly equilateral triangles. Advantageously in accordance with the invention, the second group of the orifices of the end B (32) are in the center of such triangles. This second group of orifices is preferably likewise distributed homogeneously over the cross section of the end B (32). It is advantageous in accordance with the invention when essentially all triangle centers are occupied by orifices belonging to the second group.

The space around the passages U (26) forms the collecting space (27) for the waste liquor which is conducted out of the wash column (2).

It is preferable for the process according to the invention when a flush liquid supply space (40) is present as a further space between the waste liquor collecting space (27) and the suspension distributor space (A), which can be created by incorporating an intermediate end B (41). The passages U (26) here are conducted through the intermediate end B (41) essentially with sealing. In addition, the intermediate end B** (41) has orifices (preferably circular bores (holes)), into which flush tubes (42) open, which are distributed over the cross section in the same way as the filter tubes (6) and project into a corresponding filter tube (6) down into the lower third of the particular filter element (7). The external diameter of the flush tubes (42) is, appropriately in accordance with the invention, selected such that it corresponds to 0.3 to 0.6 times the internal diameter of the filter tubes (6). In the lower third are advantageously mounted, on the outer wall of each flush tube (42), centering cams which ensure a centered position of the particular flush tube (42) in the corresponding filter tube (6).

The orifices in the end B** (41) are advantageously such that they can be closed or opened as desired. When they are closed, it is possible to feed any heating medium into the space (40) in order to melt crystalline deposits and encrustations on the end B* (39) and at the inlet into the passages U (26). When orifices in the end B** (41) are open, it is possible, for example by using heated waste liquor which has been conducted out of the wash column beforehand, to melt crystalline deposits on the filter elements F (7).

Advantageously in accordance with the invention, the procedure in the purifying removal of acrylic acid crystals from a suspension S of crystals thereof in mother liquor by means of a hydraulic wash column is such that, both in the course of startup of the separating process and in the steady-state operation thereof, a small, previously heated (to temperatures in the range from 14 to 20 or to 25° C.) substream (based on the total waste liquor flow conducted out of the hydraulic wash column, up to 40 or up to 25%, generally at least 5%) of the total waste liquor flow conducted out of the wash column is constantly passed into the corresponding filter tubes (6) as a preventative measure, distributed over all flush tubes (42), in order to prevent the formation of encrustations on the filter elements F (7) thereof. Appropriately in application terms, the aforementioned heating is undertaken by forced conveying of the substream by means of a corresponding delivery pump through an indirect heat exchanger through which a heat carrier flows (cf. FIG. 7 of EP-A 1 448 282). The filter elements F (7) are normally adjoined by the filter tube displacers (38). In the center of the process space (B) of the wash column (0) is preferably a circular cylindrical central displacer body (43). With regard to the dimensions and material properties thereof, reference is made to the remarks of EP-A 1 448 282. The central displacer body (43) is preferably secured statically on the end B (32) (which generally has no passage and no orifice in the securing region) and projects to about 1 to 20 mm above the removal device (16) (for example a bladed disk). However, it may also be bonded in a fixed manner to the bladed disk and, as a result, be configured so as to rotate with the latter. It is appropriate in application terms for lamellae (44) or elements which are equipped with orifices and run away radially from the drive shaft (18) in the crystal melt space (C) to bear (support) the removal device (bladed disk) (16).

A combination of a distributor space cone (45) and a nested arrangement of funnels (46) spaced apart from one another, arranged above the former, functions as an additional distributor space aid in the distributor space A. The necks of the funnels end in the feed stub (47) of the distributor space, and the heads of the funnels project beyond the distributor space cone. A bursting disk (48) in the delivery connection E2 (34) provides assurance against excess pressures which are impermissible for safety reasons. In the mixer (49), the delivery connection E2 (34) and the delivery connection C2 (36) are combined. Appropriately in application terms, the two delivery connections E2, C2 are combined in the form of coaxial pipelines. The suspension S is advantageously conducted in the inner of the two pipelines and the control liquor in the outer pipeline. A mixing zone upstream of entry into the feed stub ends the inner pipeline, and only the outer pipeline is then continued as what is then a common delivery connection E2, C2 to the distributor space. The inner pipeline narrows conically toward its end and functions at its end as a motive nozzle with the suspension S as the motive jet which sucks in the control liquor conducted from the outside in the adjoining mixing zone, and mixes with it as a result.

The manometer M3 is advantageously a pressure difference manometer of the 3051 CD differential membrane sensor type, measurement range: 0 to 500 mbar, from the supplier Rosemount, which enables direct access to the pressure difference between measurement points immediately above a passage U (26) in the distributor space and immediately below a passage U (26) in the process space. Otherwise, identical addresses in FIG. 2 have the same meanings as in FIG. 1.

FIG. 3 of this document shows, in qualitative terms, the profile of the pressures $P_K$ and $P_V$ and of the pressure difference $P_D$ until the time $t_s$ is passed. The abscissa shows the time ($t_S$ is generally in the range from 10 min to 2 h), and the ordinate shows the pressures in bar. In the case of the startup underlying FIG. 3, the hydraulic wash column, including the melt circuit thereof, was first filled completely with mother liquor of the suspension S to be treated as startup liquid AT.

The process according to the invention for startup of a separating process for purifying removal of acrylic acid crystals from a suspension S of crystals thereof in mother liquor is advantageous especially when the suspension S, based on the molar content of acrylic acid therein, has a comparatively high molar total content of constituents other than acrylic acid.

The process according to the invention is thus suitable especially for removing crystals of acrylic acid which originates from the product gas mixture of a heterogeneously catalyzed partial gas phase oxidation of a $C_3$ precursor compound of acrylic acid (for example propane, propylene, acrolein, propionic acid, propanol, glycerol and/or propionaldehyde) (cf., for example, WO 2004/035514, DE-A 10 2007 004960, DE-A 102 43625 and DE-A 103 23758).

Accordingly, useful suspensions S suitable in accordance with the invention are, for example, all of those disclosed in documents DE-A 10 2007 043759, WO 01/77056, DE-A 10 2007 043758, DE-A 10 2007 043748 and DE-A 10 2007 004960.

Such suspensions S may have, for example, one of the following sets of contents:
$\geq$70% by weight of acrylic acid,
up to 15% by weight of acetic acid, up to 5% by weight of propionic acid,
up to 5% by weight of low molecular weight aldehydes,
up to 3% by weight of polymerization inhibitors,
0 to 5% by weight of diacrylic acid (Michael adduct), and
up to 25% by weight of water;
or
≧80% by weight of acrylic acid,
≧100 ppm by weight to ≦10% by weight of acetic acid,
≧10 ppm by weight to ≧5% by weight of propionic acid,
up to 5% by weight of low molecular weight aldehydes,
up to 3% by weight of polymerization inhibitors,
0 to 5% by weight of diacrylic acid (Michael adduct), and
up to 10% by weight of water;
or
≧90% by weight of acrylic acid,
≧100 ppm by weight to ≦5% by weight of acetic acid,
≧10 ppm by weight to ≦2% by weight of propionic acid,
up to 2% by weight of low molecular weight aldehydes,
up to 2% by weight of polymerization inhibitors,
0 to 3% by weight of diacrylic acid (Michael adduct), and
up to 9% by weight of water;
or
≧95% by weight of acrylic acid,
≧100 ppm by weight to ≦3% by weight of acetic acid,
≧10 ppm by weight to ≦2% by weight of propionic acid,
up to 2% by weight of low molecular weight aldehydes,
up to 2% by weight of polymerization inhibitors,
0 to 2% by weight of diacrylic acid (Michael adduct), and
up to 4.9% by weight of water;
or
93 to 98% by weight of acrylic acid,
1 to 5% by weight of water,
0.001 to 3% by weight of acrolein,
≧0 to 3% by weight of methacrolein,
≧0 to 3% by weight of methacrylic acid,
0.1 to 3% by weight of acetic acid,
0.01 to 3% by weight of propionic acid,
0.001 to 3% by weight of formaldehyde,
0.001 to 3% by weight of aldehydes other than formaldehyde,
0.01 to 3% by weight of maleic acid, and
≧0 to 3% by weight of protoanemonin.

All of the above is true especially when the suspension S comprises at least 0.1% by weight of water.

Moreover, it is especially true when the suspension S comprises not more than 99% or not more than 98% by weight of acrylic acid.

It is of course also true when both aforementioned conditions are met simultaneously.

In other words, in the case of suspensions S which comprise ≧70 to ≦99% by weight of acrylic acid and ≧0.1% by weight of water (frequently ≦20% by weight or ≦10% by weight of water), the process according to the invention is employable particularly advantageously.

When a separating process for purifying removal of acrylic acid crystals from a suspension S of crystals thereof in mother liquor with a hydraulic wash column is in a steady operating state (such a state is characterized in that the operating conditions are maintained essentially unchanged as a function of the operating time), it may be necessary owing to a sudden change in market demand to increase or to lower the throughput through the hydraulic wash column in order to increase or to reduce the flow rate of the pure product stream to be discharged through the outlet A.

Normally, such an increase in throughput is necessarily associated with a rise in the flow rate of the stream of the crystal suspension S supplied to the distributor space to a new steady-state value, while the other properties of the suspension S normally remain essentially unchanged. Advantageously in application terms, such an increase in the loading of the hydraulic wash column with suspension S is implemented as follows. The increase is effected in a step size of 2 to 10% of the particular starting value. Each step is followed by a hold time of 5 to 30 min. When the position of the bed level (the buildup front) is changed, which is undesired, a corresponding adjustment of the control liquor flow is undertaken.

In the case of a lowering of the loading of a hydraulic wash column which had previously been operated in a steady operating state with suspension S (for example as a reaction to a falling demand for pure product), it is in contrast advantageously possible to proceed as follows. When lowering the loading, it is possible to undertake a lowering of up to 50% of the particular starting value in one step. Lowering with step sizes on a corresponding basis of 5 to 20% is, however, likewise possible. A subsequent wait time of 1 to 20 min. is appropriate here too, but not indispensable.

It is advisable to proceed in a corresponding manner when, additionally or alone, the degree of crystallization of the suspension S and/or the crystal size of the crystals present suspended in the suspension S changes suddenly from a steady operating state.

In order to end in a regular manner (take out of operation) a separating process in the steady operating state (i.e. all drives of the separating apparatus including all corresponding streams in the separating process (including a constant feed of heated flush liquor through all flush tubes (42)) are in operation), as described in this document, for purifying removal of acrylic acid crystals from a suspension S of crystals thereof in mother liquor with a separating apparatus comprising a hydraulic wash column (for example the apparatus shown in FIG. 2; all numerical and alphabetic addresses used hereinafter relate to FIG. 2), the sequence of the measures which should be taken for this purpose can in principle be selected freely (i.e. it is not indispensable to comply with a specific sequence of the individual steps to be taken).

Advantageously in application terms, however, the sequence stated hereinafter will be complied with for such a shutdown:

1. The first measure is to shut down the delivery pump P2 (8) which, in steady-state operation, pumps the suspension S of acrylic acid crystals in mother liquor into the distributor space (A) of the hydraulic wash column.
2. By maintaining the operation of the removal device (bladed disk) (16) and the control liquor stream conveyed by the delivery pump P3 (13) (the flow rate of which is generally maintained or increased as required (according to delivery)), the crystal bed present in the process space (B) is conducted out of it as far as possible (conducting the crystal bed out (running it out) in this way is essentially possible until areas of the filters F (7) begin to project out of the residual crystal bed still present).
3. By increasing the temperature in the crystal melt circuit (31) to values above 15° C. and ≦35° C. (for example by increasing the flow rate of the heat carrier medium fed to the heat transferer W (9)) and by further supply of flush liquor having temperatures above 15° C. and ≦35° C. through the flush liquid supply space (40) and the flush tubes (42), the crystal bed residue still remaining in the wash column when the crystal bed is run out is melted. During the melting, the removal device (16) and the delivery pump P3 (13) for the control liquor stream preferably continue to run, in order to contact the warm flush liquor more intensively with the remaining crystals and thus to promote the melting thereof.

During the further supply of warm flush liquor, advantageously in application terms, an acrylic acid stream is constantly conducted out of the crystal melt circuit through the regulable flow (10) and out of the outlet A (3) (for example into a collecting vessel; from this, this acrylic acid is, appropriately in application terms, recycled, for example, into the condensation column in which the acrylic acid to be purified by crystallization has possibly been removed from the product gas mixture of a heterogeneously catalyzed partial gas phase oxidation to prepare acrylic acid by, for example, fractional condensation; cf., for example, WO 2001/077056). In this way, increasing mixing of the already purified acrylic acid (glacial acrylic acid melt) present exclusively in the crystal melt circuit (31) on commencement of the shutdown operation with the waste liquor (mother liquor+control liquor) which comprises enriched polymerization inhibitor and is used as flush liquor is accomplished, which additionally stabilizes the crystal melt circuit and counteracts undesired free-radical polymerization of acrylic acid therein).

4. Then the supply of molecular oxygen-comprising gas and of polymerization-overinhibited glacial acrylic acid into the crystal melt circuit (31) for the purpose of stabilizing the latter during steady-stage operation is stopped.

5. During the individual steps 2 to 4, no volume flow greater than the volume flow of warm flush liquor supplied is conducted out of the outlet A (3), such that the process space of the wash column is always filled completely with condensed material. By means of temperature sensors (e.g. thermocouples), which can also be used to regulate the position of the wash front in steady-state operation, the temperature of the condensed phase which occupies the process space of the wash column is determined constantly. If these temperature sensors indicate a temperature in the range from >16° C. to 20° C. over a period of at least 5 minutes, preferably of at least 10 minutes, it can be assumed that all of the crystals still present in the wash column when the bed has been run out have melted. Now the supply of the heat carrier medium into the heat transferer W (9) is stopped. Thereafter, the removal device (16) and the delivery pump P3 (13) for the control liquor stream and the delivery pump P1 (11) for the crystal melt circuit (31) are stopped.

6. Then the supply of warm flush liquor is ended.

7. The liquid (liquid acrylic acid) present in the wash column is then discharged until it is completely empty (for example, an emptying valve can be mounted on the stub at the lower end (to the right) in FIG. 2, by means of which emptying is effected).

The wash column which has thus been put out of operation and completely emptied can later be put back into operation in accordance with the inventive procedure.

At this point, it should be emphasized that the melting of the residual crystal bed not discharged from the wash column, in the shutdown operation, can also be undertaken by an appropriate input of warm water (e.g. 20 to 25° C.). The warm water input may be undertaken directly into the crystal melt circuit or in the form of "control liquor" and/or in the form of "flush liquor".

If it is necessary to take out of operation (end) a separating process in the steady operating state, as described in this document, for purifying removal of acrylic acid crystals from a suspension S of crystals thereof in mother liquor with a separating apparatus comprising a hydraulic wash column (for example the apparatus shown in FIG. 2) owing to a sudden operating fault, preference is likewise given to employing the sequence of steps 1 to 7 detailed above for regular (normal) ending. If one step or another cannot be performed owing to the fault, it is regularly omitted and the shutdown is typically continued with the next step listed in numeral order. If, for example, the crystal bed cannot be very substantially run out of the process space of the hydraulic wash column owing to a fault in the removal device (16) or the delivery pump P3 (13) for the conveying of the control liquor stream, step 2 is omitted and all of the crystal bed still present in the wash column is melted according to step 3 to 5 of the sequence. In each case, it is, however, appropriate in application terms to shut down the delivery pump P2 (8) as the first measure (as the first step) of the shutdown, and hence to prevent the delivery of suspension S of acrylic acid crystals in mother liquor into the distributor space (A) of the hydraulic wash column.

If, owing to the operating fault which has occurred, there is no means of heat input by means of the heat transferer W (9) and by means of heated flush liquor supplied through the flush tubes (42), crystals which are still present in the wash column and have not been run out in step 2, owing to the fact that there is no longer any cold input by supply of suspension S, can also be melted gradually by the natural heat input of the running delivery pumps P3 (13) for the control liquor stream and/or P1 (11) for the crystal melt circuit (31).

Generally, in a shutdown, the presence of glacial acrylic acid having an elevated temperature ($\geq 20°$ C. or $\geq 25°$ C.) in the crystal melt circuit should be avoided in the course of the shutdown (of the rundown). In addition, liquid acrylic acid remaining in the wash column, without being exchanged, over prolonged periods (several days) even $\geq 2$ days may be critical) up to several weeks) after the shutdown should be avoided.

If the steady operating state of the wash column is disrupted only briefly, such that the crystal bed in the process space of the wash column is still intact after the fault has ended (is in the continuous state), operation preferably continues as follows.

If the operating state which follows is not already present, it is established in the sequence specified hereinafter.

1. Delivery pump P2 (8), the removal device (16) and the delivery pump P3 (13) are shut down. The supply of warm flush liquor through the flush tubes (42) is maintained. The regulable flow (10) to the outlet A (3) is closed. The heat transferer W (9) and the pump P1 (11) of the crystal melt circuit (31) and the metered addition of the molecular oxygen and inhibitor solution to the crystal melt circuit (31) are in operation.

2. Switch on the removal device (16).

3. Switch on the delivery pump P2 (8) for the crystal suspension S.

4. Switch on the delivery pump P3 (13) for the control liquor stream.

5. Slowly open the regulable flow (10) to the outlet A (3) in order to establish (ensure) an appropriately high position of the wash front (37).

The present application thus comprises especially the following inventive embodiments:

1. A process for starting up a separating process for purifying removal of acrylic acid crystals from a suspension S of crystals thereof in mother liquor with an apparatus which comprises a hydraulic wash column which has a process space which is rotationally symmetric with respect to its longitudinal axis running from the top downward and is bounded by a cylindrical outer wall and two opposite ends on the axis of symmetry, in which
one or more filter tubes extend through the process space from the upper end of the process space parallel to the longitudinal axis thereof, which run toward the lower end of the process space opposite the upper end, and have, in the half of the process space toward the lower end of the process space, at least one filter F which constitutes the only direct connection between the particular filter tube interior and the process space, and are conducted out of the wash column outside the process space,
the quotient Q=L/D of the distance L between the upper and lower ends of the process space and the diameter D of the process space is 0.3 to 4,
the lower end of the process space is followed in the downward direction by the crystal melt space of the wash column, a rotatable removal device being integrated between the two spaces and a crystal melt circuit which is conducted through the crystal melt space comprising, outside the crystal melt space,
a delivery pump P1 which is outside the wash column and has a suction side and a pressure side,
a first delivery connection G1 which leads from the crystal melt space of the wash column to the suction side of the delivery pump P1,
a second delivery connection G2 which leads from the pressure side of the delivery pump P1 back into the crystal melt space of the wash column and has an outlet A from the crystal melt circuit with regulable flow, and
a heat transferer W, through which either the delivery connection G1 from the crystal melt space to the suction side of the delivery pump P1 or the delivery connection G2 from the pressure side of the delivery pump P1 to the crystal melt space is conducted,
connected upstream of the upper end of the process space in the upward direction is a distributor space which is separated from the process space at least by one end B which has passages U which lead into the process space on the side of the end B facing the process space and into the distributor space on the side of the end B facing away from the process space,
a delivery pump P2 which has a suction side and a pressure side and a source QS of the suspension S are present outside the wash column,
a first delivery connection E1 leading from the source QS to the suction side of the delivery pump P2, and
a second delivery connection E2 leading from the pressure side of the delivery pump P2 into the distributor space,
a delivery pump P3 which has a suction side and a pressure side and a source QT of a control liquor are optionally present outside the wash column,
a first delivery connection C1 leading from the suction side of the pump P3 to the source QT, and
a second delivery connection C2 leading from the pressure side of the pump P3 into the distributor space and/or into the longitudinal section of the process space between the upper end thereof and the filters F of the filter tubes,
and in which, in the course of performance of the separating process, in steady-state operation thereof,
the pump P2 is used to continuously conduct a stream ST of the suspension S from the source QS through the delivery connections E1, E2 via the distributor space and through the passages U into the process space of the wash column,
optionally, the pump P3 is used to conduct a stream SL of the control liquor from the source QT through the delivery connections C1, C2 via the distributor space and the passages U and/or directly into the process space of the wash column,
overall, a stream SM comprising mother liquor and optionally control liquor is conducted as waste liquor stream into the filter tube interior via the filters F of the filter tubes, and out of the wash column via the filter tubes, and this waste liquor stream SM conducted out of the wash column is used as the source QT for the control liquor,
the conduction of mother liquor and optionally control liquor in the process space of the wash column maintains the development of a crystal bed of acrylic acid crystals which has a buildup front facing the upper end of the process space, at which crystals of the stream ST of the suspension S supplied are added continuously onto the crystal bed,
the crystal bed is conveyed from the top downward past the filters F to the rotating removal device by the force which results from the hydraulic flow pressure drop of the conduction of mother liquor and optionally control liquor in the process space,
the rotating removal device removes acrylic acid crystals from the crystal bed which meets it,
the stream of the acrylic acid crystals removed is conveyed through the rotating removal device and/or past the rotating removal device into the crystal melt space which follows downstream of the process space in conveying direction of the crystal bed, and melted in the crystal melt circuit conducted through the crystal melt space as a result of introduction of heat with the heat transferer W to give a crystal melt stream, and
the flow through the outlet A is regulated such that, based on the flow rate of the aforementioned crystal melt stream, proceeding from the crystal melt space, a substream of crystal melt flows as wash melt stream through the rotating removal device and/or past the rotating removal device against the direction of movement of the crystal bed back into the process space, where it ascends within the crystal bed conveyed downward and in doing so washes the mother liquor off the crystals and forces it back, said mother liquor remaining in the crystal bed having been conveyed with the latter under the filters F, which forms, in the longitudinal section of the process space which extends from the filters F to the lower end of the process space, in the crystal bed, a wash front which divides the crystal bed, from the top downward, into a mother liquor zone and into a wash melt zone, and the remaining substream of the aforementioned crystal melt stream leaves the crystal melt circuit through the outlet A,
wherein, in the course of startup of the separating process for first development of the crystal bed in the process space,
the crystal melt circuit comprising the crystal melt space, and the process space of the previously unfilled wash column, are at first filled with an acrylic acid-comprising startup liquid AT such that the fill height of the startup liquid AT in the process space overtops at least the removal device, then the filling of the wash column is continued by using the pump P2 to conduct a stream ST* of the suspension S from the source QS through the delivery connections E1, E2 via the distributor space and through the passages U into the process space of the wash column and optionally using the pump P3 to conduct a substream of the waste liquor stream SM* conducted out of the wash column through the filter tubes as source QT*, as control liquor stream SL* through the delivery connections C1, C2 via the distributor space and the passages U and/or directly into the process space of the wash column, at least until the time $t_s$ is attained at which the pressure difference $P_D = P_K - P_V$, where $P_K$ is the pressure existing at any desired point in the crystal melt space at a particular time in the supply of the stream ST* and $P_V$ is the pressure which exists at the same time at any desired point in the distributor space, no longer rises or remains constant as a function of the duration of the supply of the stream ST*, but decreases suddenly, with the proviso that until the time $t_S$, the mean superficial velocity on the filters F, calculated as the arithmetic mean of the total waste liquor flow SM* which flows at the particular time through the filters F of the filter tubes during the supply of the stream ST*, divided by the total area of all filters F, is not more than 80 m³/(m²·h), the acrylic acid-comprising startup liquid AT is one from which, in the course of cooling until crystallization sets in, the crystals which form in the course of crystallization are acrylic acid crystals, and between the crystal formation temperature $T^{KB}$, reported in degrees Celsius, of these acrylic acid crystals in the startup liquid AT and the temperature $T^S$, reported in degrees Celsius, of the suspension S of the stream ST*, the following relationship is satisfied:

$$T^{KB} \leq T^S + 15° C.$$

2. A process according to embodiment 1, wherein the mean superficial velocity on the filters F until the time $t_S$ is not more than 75 m³/(m²·h).
3. A process according to embodiment 1, wherein the mean superficial velocity on the filters F until the time $t_S$ is not more than 70 m³/(m²·h).
4. A process according to any of embodiments 1 to 3, wherein the mean superficial velocity on the filters F until the time $t_s$ is at least 5 m³/(m²·h).
5. A process according to any of embodiments 1 to 3, wherein the mean superficial velocity on the filters F until the time $t_s$ is at least 10 m³/(m²·h).
6. A process according to any of embodiments 1 to 3, wherein the mean superficial velocity on the filters F until the time $t_s$ is at least 15 m³/(m²·h).
7. A process according to any of embodiments 1 to 3, wherein the mean superficial velocity on the filters F until the time $t_s$ is at least 20 m³/(m²·h).
8. A process according to any of embodiments 1 to 7, wherein the mean superficial velocity on the filters F until the time $t_S$ is not more than 60 m³/(m²·h).
9. A process according to any of embodiments 1 to 7, wherein the mean superficial velocity on the filters F until the time $t_s$ is not more than 50 m³/(m²·h).
10. A process according to any of embodiments 1 to 9, wherein the quotient Q is $\geq 0.5$.
11. A process according to any of embodiments 1 to 9, wherein the quotient Q is $\geq 0.7$.
12. A process according to any of embodiments 1 to 11, wherein the quotient Q is $\leq 3.5$.
13. A process according to any of embodiments 1 to 11, wherein the quotient Q is $\leq 3$.
14. A process according to any of embodiments 1 to 11, wherein the quotient Q is $\leq 2.5$.
15. A process according to any of embodiments 1 to 11, wherein the quotient Q is $\leq 2$.
16. A process according to any of embodiments 1 to 15, wherein the distance L is $\geq 0.5$ m.
17. A process according to any of embodiments 1 to 15, wherein the distance L is $\geq 0.8$ m.
18. A process according to any of embodiments 1 to 15, wherein the distance L is $\geq 1$ m.
19. A process according to any of embodiments 1 to 8, wherein the distance L is $\leq 5$ m.
20. A process according to any of embodiments 1 to 8, wherein the distance L is $\leq 4$ m.
21. A process according to any of embodiments 1 to 8, wherein the distance L is $\leq 3$ m.
22. A process according to any of embodiments 1 to 21, wherein the relationship $T^{KB} \leq T^S + 10°$ C. is satisfied.
23. A process according to any of embodiments 1 to 21, wherein the relationship $T^{KB} \leq T^S + 5°$ C. is satisfied.
24. A process according to any of embodiments 1 to 23, wherein $T^{KB}$ is not more than 20° C. below $T^S$.
25. A process according to any of embodiments 1 to 23, wherein $T^{KB}$ is not more than 10° C. below $T^S$.
26. A process according to any of embodiments 1 to 23, wherein $T^{KB}$ is not more than 5° C. below $T^S$.
27. A process according to any of embodiments 1 to 26, wherein the startup liquid AT is mother liquor removed from the suspension S.
28. A process according to any of embodiments 1 to 26, wherein the startup liquid AT is the melt of crystals removed from the suspension S.
29. A process according to any of embodiments 1 to 26, wherein the startup liquid AT is molten suspension S.
30. A process according to any of embodiments 1 to 26, wherein the startup liquid AT is that liquid from which the suspension S is obtained by cooling.
31. A process according to any of embodiments 1 to 26, wherein the startup liquid AT is a mixture of at least two of the startup liquids AT specified in embodiments 27 to 30.
32. A process according to any of embodiments 1 to 31, wherein, at least over 50% of the period calculated from the commencement of supply of the stream ST* of the suspension S until the time $t_S$ is reached, the superficial velocity on the filters F which exists at the particular time is not more than 80 m³/(m²·h).
33. A process according to any of embodiments 1 to 31, wherein, at least over 50% of the period calculated from the commencement of supply of the stream ST* of the suspension S until the time $t_S$ is reached, the superficial velocity on the filters F which exists at the particular time is not more than 70 m³/(m²·h).
34. A process according to any of embodiments 1 to 31, wherein, at least over 50% of the period calculated from the commencement of supply of the stream ST* of the suspension S until the time $t_S$ is reached, the superficial velocity on the filters F which exists at the particular time is not more than 60 m³/(m²·h).
35. A process according to any of embodiments 1 to 31, wherein, at least over 75% of the period calculated from the commencement of supply of the stream ST* of the suspension S until the time $t_S$ is reached, the superficial velocity on the filters F which exists at the particular time is not more than 80 m³/(m²·h).

36. A process according to any of embodiments 1 to 31, wherein, at least over 75% of the period calculated from the commencement of supply of the stream ST* of the suspension S until the time $t_S$ is reached, the superficial velocity on the filters F which exists at the particular time is not more than 70 m³/(m²·h).

37. A process according to any of embodiments 1 to 31, wherein, at least over 75% of the period calculated from the commencement of supply of the stream ST* of the suspension S until the time $t_S$ is reached, the superficial velocity on the filters F which exists at the particular time is not more than 60 m³/(m²·h).

38. A process according to any of embodiments 1 to 31, wherein, over the entire period calculated from the commencement of supply of the stream ST* of the suspension S until the time $t_S$ is reached, the superficial velocity on the filters F which exists at the particular time is not more than 80 m³/(m²·h).

39. A process according to any of embodiments 1 to 31, wherein, over the entire period calculated from the commencement of supply of the stream ST* of the suspension S until the time $t_S$ is reached, the superficial velocity on the filters F which exists at the particular time is not more than 70 m³/(m²·h).

40. A process according to any of embodiments 1 to 31, wherein, over the entire period calculated from the commencement of supply of the stream ST* of the suspension S until the time $t_S$ is reached, the superficial velocity on the filters F which exists at the particular time is not more than 60 m³/(m²·h).

41. A process according to any of embodiments 1 to 40, wherein, at least over 50% of the period calculated from the commencement of supply of the stream ST* of the suspension S until the time $t_S$ is reached, the superficial velocity on the filters F which exists at the particular time is at least 5 m³/(m²·h) or at least 10 m³/(m²·h).

42. A process according to any of embodiments 1 to 40, wherein, at least over 75% of the period calculated from the commencement of supply of the stream ST* of the suspension S until the time $t_S$ is reached, the superficial velocity on the filters F which exists at the particular time is at least 5 m³/(m²·h) or at least 10 m³/(m²·h).

43. A process according to any of embodiments 1 to 40, wherein, over the entire period calculated from the commencement of supply of the stream ST* of the suspension S until the time $t_S$ is reached, the superficial velocity on the filters F which exists at the particular time is at least 5 m³/(m²·h) or at least 10 m³/(m²·h).

44. A process according to any of embodiments 1 to 43, wherein, over the entire period calculated from the commencement of supply of the stream ST* of the suspension S until the time $t_S$ is reached, the arithmetic mean M of the total flow of liquid supplied to the process space of the wash column, divided by the free cross-sectional area of the process space, is 1 to 30 m³/(m²·h).

45. A process according to embodiment 44, wherein the arithmetic mean M divided by the free cross-sectional area of the process space is 5 to 25 m³/(m²·h).

46. A process according to any of embodiments 1 to 45, wherein, at least over 50% of the period calculated from the commencement of supply of the stream ST* of the suspension S until the time $t_S$ is reached, the total flow of liquid supplied to the process space of the wash column at the particular time, divided by the free cross-sectional area of the process space, is 1 to 30 m³/(m²·h) or 5 to 25 m³/(m²·h).

47. A process according to any of embodiments 1 to 45, wherein, at least over 75% of the period calculated from the commencement of supply of the stream ST* of the suspension S until the time $t_S$ is reached, the total flow of liquid supplied to the process space of the wash column at the particular time, divided by the free cross-sectional area of the process space, is 1 to 30 m³/(m²·h) or 5 to 25 m³/(m²·h).

48. A process according to any of embodiments 1 to 45, wherein, over the entire period calculated from the commencement of supply of the stream ST* of the suspension S until the time $t_S$ is reached, the total flow of liquid supplied to the process space of the wash column at the particular time, divided by the free cross-sectional area of the process space, is 1 to 30 m³/(m²·h) or 5 to 25 m³/(m²·h).

49. A process according to any of embodiments 1 to 48, wherein the content of acrylic acid in the suspension S is ≧70% by weight.

50. A process according to any of embodiments 1 to 48, wherein the content of acrylic acid in the suspension S is ≧80% by weight.

51. A process according to any of embodiments 1 to 48, wherein the content of acrylic acid in the suspension S is ≧90% by weight.

52. A process according to any of embodiments 1 to 51, wherein the content of acrylic acid in the suspension S is ≦99% by weight.

53. A process according to any of embodiments 1 to 52, wherein the degree of crystallization of the suspension S is ≧0.10.

54. A process according to any of embodiments 1 to 52, wherein the degree of crystallization of the suspension S is ≧0.20.

55. A process according to any of embodiments 1 to 52, wherein the degree of crystallization of the suspension S is ≧0.25.

56. A process according to any of embodiments 1 to 55, wherein the degree of crystallization of the suspension S is ≦0.60.

57. A process according to any of embodiments 1 to 55, wherein the degree of crystallization of the suspension S is ≦0.50.

58. A process according to any of embodiments 1 to 57, wherein the longest dimension of the majority of acrylic acid crystals present in the suspension S is 50 to 1600 μm.

59. A process according to any of embodiments 1 to 57, wherein the longest dimension of the majority of acrylic acid crystals present in the suspension S is 200 to 900 μm.

60. A process according to any of embodiments 1 to 59, wherein the orifice ratio OV of the removal device is ≧0.01.

61. A process according to any of embodiments 1 to 59, wherein the orifice ratio OV of the removal device is ≧0.03.

62. A process according to any of embodiments 1 to 59, wherein the orifice ratio OV of the removal device is ≦0.9.

63. A process according to any of embodiments 1 to 62, wherein the removal device is a bladed disk having passage orifices.

64. A process according to any of embodiments 1 to 63, wherein, based on the total volume of the crystal melt circuit, 30 to 60% by volume is accounted for by the volume of the crystal melt space.

65. A process according to any of embodiments 1 to 64, wherein the crystal melt circuit and the process space of the previously unfilled wash column are at first filled with an acrylic acid-comprising startup liquid AT such that the fill height of the startup liquid AT in the process space overtops at least the filters F.

66. A process according to embodiment 65, wherein the fill height of the startup liquid AT extends at least to the midpoint of the distance L from the lower to the upper end of the process space.

67. A process according to embodiment 65, wherein the fill height of the startup liquid AT extends at least to the last quarter of the distance L from the lower to the upper end of the process space.

68. A process according to embodiment 65, wherein the fill height of the startup liquid AT extends at least to the upper end of the process space.

69. A process according to embodiment 65, wherein the fill height of the startup liquid AT projects beyond the process space into the distributor space and fills at least half the volume thereof.

70. A process according to embodiment 65, wherein the fill height of the startup liquid AT projects beyond the process space into the distributor space and fills the volume thereof completely.

71. A process according to any of embodiments 1 to 70, wherein the heat transferer W is a tube bundle heat transferer.

72. A process according to any of embodiments 1 to 71, wherein the temperature of the suspension S is −25 to +14° C.

73. A process according to any of embodiments 1 to 71, wherein the temperature of the suspension S is −5 to +12° C.

74. A process according to any of embodiments 1 to 71, wherein the temperature of the suspension S is +4 to +9° C.

75. A process according to any of embodiments 1 to 74, wherein the mother liquor present in the suspension S comprises $\geq 70\%$ by weight or $\geq 80\%$ by weight of acrylic acid.

76. A process according to any of embodiments 1 to 75, wherein the mother liquor present in the suspension S comprises $\leq 99\%$ by weight of acrylic acid.

77. A process according to any of embodiments 1 to 76, wherein a substream of the waste liquor stream SM* conducted out of the wash column through the filter tubes as source QT* is conducted with the pump P3 as control liquor stream SL* through the delivery connections C1, C2 via the distributor space and through the passages U into the process space of the wash column.

78. A process according to any of embodiments 1 to 77, wherein the delivery connections E2 and C2 upstream of the supply space of the hydraulic wash column are designed as coaxial pipelines, the inner pipeline ending upstream of the supply space in flow direction, and only the outer pipeline being continued as a common delivery connection E2, C2 up to the distributor space.

79. A process according to embodiment 78, wherein the cross section of the inner pipeline narrows toward the end thereof.

80. A process according to embodiment 78 or 79, wherein the suspension S flows within the inner pipeline.

81. A process according to any of embodiments 1 to 80, wherein both the pressure $P_K$ and the pressure $P_V$ are measured during the startup.

82. A process according to any of embodiments 1 to 81, wherein the pressure difference $P_D$ is determined with a pressure difference manometer.

83. A process according to any of embodiments 1 to 82, wherein, from commencement of the supply of the stream ST* of the suspension S until the time $t_S$ is reached, the heat exchanger W is not in operation.

84. A process according to any of embodiments 1 to 83, wherein, from commencement of the supply of the stream ST* of the suspension S until the time $t_S$ is reached, the delivery pump P1 is not in operation.

85. A process according to any of embodiments 1 to 84, wherein, from commencement of the supply of the stream ST* of the suspension S until the time $t_S$ is reached, the rotatable removal device is not put into operation.

86. A process according to any of embodiments 1 to 85, wherein, from commencement of the supply of the stream ST* of the suspension S until the time $t_S$ is reached, the flow through the outlet A is blocked.

87. A process according to any of embodiments 1 to 86, wherein, after the time $t_S$, the melt circuit and the removal device are put into operation and the flow through the outlet A is opened, and a molecular oxygen-comprising gas is metered into the melt circuit, by introducing the molecular oxygen-comprising gas into a substream of the melt circuit, and then supplying the substream comprising the molecular oxygen back to the melt circuit.

88. A process according to embodiment 87, wherein, before the molecular oxygen-comprising substream is supplied back to the melt circuit, gas undissolved in the substream is removed in a gas separator.

89. A process according to any of embodiments 1 to 88, wherein the process space of the hydraulic wash column has a central displacer body.

90. A process according to any of embodiments 1 to 89, wherein the height of the passages U is 200 to 1000 mm.

91. A process according to any of embodiments 1 to 90, wherein the orifices of the passages U which lead into the process space or into the distributor space have a cross-sectional area which, based on a circular shape of the orifice, corresponds to a diameter of 15 to 300 mm.

92. A process according to any of embodiments 1 to 91, wherein the ratio of the total area of all orifices of the passages U facing the process space to the total area of the process space cross section is 0.10 to 0.60.

93. A process according to any of embodiments 1 to 92, wherein the number of filter tubes in the hydraulic wash column is 3 to 200.

94. A process according to any of embodiments 1 to 93, wherein the internal diameter of the filter tubes is 5 to 200 mm.

95. A process according to any of embodiments 1 to 93, wherein the internal diameter of the filter tubes is 20 to 80 mm.

96. A process according to any of embodiments 1 to 95, wherein the suspension S has the following contents:
$\geq 70\%$ by weight of acrylic acid,
up to 15% by weight of acetic acid,
up to 5% by weight of propionic acid,
up to 5% by weight of low molecular weight aldehydes,
up to 3% by weight of diacrylic acid, and
up to 25% by weight of water.

97. A process according to any of embodiments 1 to 96, wherein the suspension S comprises at least 0.1% by weight of water.
98. A process according to any of embodiments 1 to 97, wherein the process for startup is followed by a separating process for purifying removal of acrylic acid crystals from the suspension S of crystals thereof in mother liquor in the hydraulic wash column put into operation.
99. A separating process for purifying removal of acrylic acid crystals from a suspension S of crystals thereof in mother liquor with an apparatus which comprises a hydraulic wash column, wherein the separating process has been put into operation by a process of embodiments 1 to 97.
100. A process according to embodiment 98 or 99, which is followed by a further process in which removed and molten acrylic acid crystals are subjected to a polymerization with acrylic acid itself or other, at least monoethylenically unsaturated compounds.

EXAMPLES AND COMPARATIVE EXAMPLES

Comparative Example 1

Process for Startup of a Hydraulic Wash Column with L/D=4.7 with a Mean Filter Superficial Velocity of 119 m$^3$/(m$^2$·h)

By fractionally condensing the product gas mixture of a two-stage heterogeneously catalyzed gas phase partial oxidation of propylene of chemical-grade purity, performed as described in WO 08/090190, 1.5 t of a crude acrylic acid per hour were removed via the side draw of the condensation column, which had the following contents:
  96.1% by weight of acrylic acid,
  446 ppm by weight of acrolein,
  20 ppm by weight of allyl acrylate,
  3764 ppm by weight of diacrylic acid,
  7460 ppm by weight of acetic acid,
  6719 ppm by weight of furfural,
  7131 ppm by weight of benzaldehyde,
  751 ppm by weight of propionic acid,
  91 ppm by weight of phenothiazine,
  247 ppm by weight of MEHQ, and
  0.83 ppm by weight of water.

By continuously adding 31 kg/h of water to the crude acrylic acid, the water content thereof was increased to 2.8% by weight. This "aqueous" crude acrylic acid was subsequently supplied to a suspension crystallizer with a temperature of 20° C. The suspension crystallizer used was a cooling disk crystallizer from GMF (the Netherlands) with a capacity of 2500 l. The crystallizer comprised an equidistantly spaced arrangement of 7 wiped cooling disks which had a homogeneous diameter of 1.25 m.

The coolant conducted through the cooling disks was a stream of a mixture of 70% by volume of water and 30% by volume of glycol, with a feed temperature of 0.5 to 1° C. The aqueous crude acrylic acid and the coolant were conducted through the crystallizer in countercurrent, viewed over the latter. The suspension of acrylic acid crystals in mother liquor conducted out of the suspension crystallizer had a degree of crystallization of 0.24 and a temperature of 6.9 to 7.0° C.

The crystal suspension thus obtained flowed out of the suspension crystallizer over an overflow weir into a stirred heatable collecting vessel. The crystals of the suspension were melted again therein, and the resulting "aqueous" crude acrylic acid was recycled back into the fractional condensation (above the side draw withdrawal).

In this way, a stream of acrylic acid crystal suspension was available, which was used to start up the hydraulic wash column described hereinafter. Additionally available was crystal suspension which had been melted again in the collecting vessel as startup liquid AT (it had a temperature of 17° C.).

The hydraulic wash column had essentially the design according to FIG. 1 of this document. The internal diameter D of the circular cylindrical process space (B) was 263 mm. The thickness of the outer wall was 5 mm. The material of manufacture was stainless steel (DIN material 1.4571). The length L of the process space (B) was 1230 mm (measured from the upper edge of the bladed disk used as the removal device (16)). The process space (B) had only one filter tube (6), which was manufactured from the same stainless steel and ran from the top downward in the center of the process space cross section. The wall thickness of the circular cylindrical filter tube (6) was 2 mm. Its external diameter was 48 mm. The total length of the filter tube (6) (including displacer (38)) was 1225 mm. The active filter length (height) was 60 mm. The upper edge of the filter F (7) was at a filter tube length of 965 mm (measured from the top downward). The process space (B) was preceded upstream by a distributor space (A) whose height was 250 mm. Process space (B) and distributor space (A) were separated from one another by an end B (32) of thickness 250 mm (in the end interior was the waste liquor collecting space (27)). Distributed homogeneously over the end B (32) were 3 passages U (26) which connected the two spaces with circular orifices of diameter 26 mm and with a constant cross section over the passage zone.

First, the hydraulic wash column (0) was filled completely with the startup liquid AT at 17° C. from the collecting vessel (melt circuit (31)+process space (B)+distributor space (A)+the delivery connections E2 (34), C2 (36), C1 (35)+the delivery pump P3 (13)). The filling was effected through a T-piece in the crystal melt circuit.

Subsequently, the delivery pump P3 (13) was put into operation and its speed was adjusted such that it sucked in a flow of 400 kg/h of the startup liquid AT through the delivery connection C1 (35) and conveyed it in the following circuit: suction side of the delivery pump P3—pressure side of the delivery pump P3—delivery connection C2 (36)—distributor space (A)—process space (B)—filter F (7)—filter tube (16)—delivery connection C1 (35) (outlet A (3) was closed).

Then (with the outlet A (3) still closed and the removal device (16) (bladed disk) not in operation and melt circuit (31) not in operation), the delivery pump P2 (8) was put into operation and this was used to withdraw, from the suspension crystallizer, via a withdrawal stub, 1000 kg/h of the suspension S of acrylic acid crystals in mother liquor, which were pumped via the delivery connection E2 (34), in addition to the abovementioned flow of 400 kg/h, into the distributor space (A) of the hydraulic wash column (0). With delivery pumps P2 (8) and P3 (13) which were thus in operation, the crystal bed developed in the process space (B) of the hydraulic wash column (0) (760 kg/h of waste liquor flowed out of the outlet (2) of the wash column apparatus). This was accompanied by an at first parallel rise in the pressures measured with the membrane manometers M1 (pressure in the distributor space (A)) and M2 (pressure in the crystal melt space (C)).

The waste liquor flow which flowed through the filter F (7) was 1080 l/h, which corresponds to a (mean) filter superficial velocity of 119 m$^3$/(m$^2$·h). After $t_S$=14 min (calculated from commencement of the startup of the delivery pump P2 (8)), the pressure $P_K$ recorded with the membrane manometer M2 suddenly began to fall, while the pressure $P_V$ detected with the membrane manometer M1 continued to rise, which corresponded to a first fall in the pressure difference $P_D=P_K-P_V$.

Immediately after the pressure change, the delivery pumps P2 (8) and P3 (13) (in that sequence) were switched off, and the delivery pump P1 (11) and the rotation of the bladed disk (16) (in that sequence) were put into operation. Subsequently, the delivery pumps P2 (8) (with a delivery output of 1000 kg/h) and the delivery pump P3 (13) (with a delivery output of 800 kg/h) were put into operation again, which set the crystal bed including buildup front in downward motion.

Then the heat transferer W (9) was put into operation, as was the metered addition of inhibiting air and pure melt solution comprising 1.5% by weight of MEHQ (solution of MEHQ in pure product removed correspondingly beforehand) into the melt circuit. As a result of subsequent partial opening of the flow through the outlet A (3), starting up the regulation of the temperature of the melt circuit (the corresponding temperature sensor was present just beyond the outlet of the heat transferer W in flow direction), starting up the regulation of the position of the buildup front (25) (of the level of the crystal bed) according to WO 2006/111565, and starting up the regulation of the wash front position (37) (the corresponding target temperature was 11.0° C.), the separating process put into operation was transferred, as described in the description, to a steady operating state, in which the buildup front (25) was 690 to 790 mm above the bladed disk (16) and the wash front (37) approx. 80 mm below the lower edge of the filter F (7). The flow of suspension S supplied for that purpose was 800 to 1400 kg/h and the control liquor flow was 400 to 1600 kg/h. Over a period of 14 days, the separating process was continued essentially without disruption.

Comparative Example 2

Process for Startup of a Hydraulic Wash Column with L/D=4.7 at a Mean Filter Superficial Velocity of 67 m³/(m²·h)

The same hydraulic wash column as in comparative example 1 was used. The suspension S was prepared and the startup liquid AT was generated likewise as described in comparative example 1.

The process for startup differed from the startup process in comparative example 1 merely in that the delivery pump P3 (13) until the time $t_S$ was set to a delivery output of 200 kg/h, and the delivery pump P2 (8) to a delivery output of 600 kg/h. The waste liquor flow which flowed through the filter F (7) was 610 l/h. This corresponds to a (mean) filter superficial velocity of 67 m³/(m²·h). After $t_S$=27 min (calculated from commencement of the startup of the delivery pump P2 (8)), the pressure $P_K$ detected with the membrane manometer M2 began to fall suddenly, while the pressure $P_V$ detected with the membrane manometer M1 continued to rise, which corresponded to a first fall in the pressure difference $P_D=P_K-P_V$.

Subsequently, the further operation was as in comparative example 1. When the delivery pump P2 (8) was restarted, the delivery output thereof was set to 1000 kg/h, and the delivery pump P3 (13) to a delivery output of 800 kg/h. The separating process which had been put into operation was transferred smoothly to a steady operating state, in which the buildup front (25) was 690 to 790 mm above the bladed disk (16) and the wash front (37) approx. 80 mm below the lower edge of the filter F (7). The corresponding flow of suspension S was 800 to 1400 kg/h and the control liquor flow was 400 to 1600 kg/h. Over a period of 14 days, the separating process was continued essentially without disruption.

Comparative Example 3

Process for Startup of a Hydraulic Wash Column with L/D=1.07 at a Mean Filter Superficial Velocity of 92 m³/(m²·h)

By fractionally condensing the product gas mixture of a two-stage heterogeneously catalyzed gas phase partial oxidation of propylene of chemical-grade purity, performed as described in WO 08/090190, 75 t per hour of a crude acrylic acid were removed via the side draw of the condensation column, which had the following contents:

96.7716% by weight of acrylic acid,
0.8253% by weight of acetic acid,
1.6640% by weight of water,
0.0213% by weight of formic acid,
0.0018% by weight of formaldehyde,
0.0070% by weight of acrolein,
0.0681% by weight of propionic acid,
0.1642% by weight of furfurals,
0.0027% by weight of allyl acrylate,
0.0012% by weight of allyl formate,
0.0164% by weight of benzaldehyde,
0.1052% by weight of maleic anhydride,
0.3278% by weight of diacrylic acid,
0.0050% by weight of phenothiazine,
0.0180% by weight of MEHQ, and
0.0002% by weight of molecular oxygen.

The crude acrylic acid conducted out of the condensation column via side draw was cooled to a temperature of 17° C. in a multistage process by indirect heat exchange (inter alia, thermally integrated with mother liquor (waste liquor) which was recycled into the condensation column and had been removed beforehand as described in this comparative example 3). Then 1230 kg/h of water at a temperature of 22° C. were added to the cooled crude acrylic acid. The resulting "aqueous" crude acrylic acid was subsequently divided into three substreams of equal size and each of the three substreams was conducted into one of three identical cooling disk suspension crystallizers operated in parallel (cf. WO 2006/111565).

These crystallizers each comprised a trough with a capacity of 65 000 l in which 24 wiped circular cooling disks were arranged in suspended succession with an equidistant separation of 30±1 cm. The diameter thereof was a uniform 3.3 m. The coolant conducted through each of the cooling disks was a stream of a mixture of 65% by weight of water and 35% by weight of glycol. The aqueous crude acrylic acid and the coolant were conducted through the particular suspension crystallizer, viewed over the latter. The coolant was divided in each case into two substreams of equal size, each of which flowed only through half of the cooling disks of the particular crystallizer. The procedure was that the particular substream was passed on from the cooling disk that it flowed through to the next cooling disk but one. One substream thus led through the even-numbered cooling disks, while the other substream flowed through the odd-numbered cooling disks (each in the manner of a series connection; the numbering of the cooling disks beginning with "1" at the first cooling plate in flow direction of the coolant). The flow rate of the particular substream was (based on a crystallizer) 95 to 105 t/h. The temperature of the coolant on entry into the foremost cooling disk in flow direction in each case was 2.5° C. The wall thickness of the cooling surfaces of the cooling disks, which were manufactured from stainless steel, was 4 mm. The wiping of the cooling disks suppressed the formation of crystalline deposits on the cooling surfaces.

The suspension of acrylic acid crystals in mother liquor conducted out of each of the three suspension crystallizers had a temperature of 7.0 to 7.1° C. and a degree of crystallization of 0.25. The speed of the cooling disk wipers was 5 revolutions per minute. The wipers were segmented in radial direction (4 segments). The wiper material used was Ultra High Molecular Weight Polyethylene.

In the rearmost part of the particular suspension crystallizer in conveying direction of the crystal suspension which forms (beyond the last cooling disk), the crystal suspension formed flowed in each case over an overflow weir into a stirred buffer vessel common to all three crystallizers (cf. DE-A 10 2007 043759). From this buffer vessel, 33 to 37 t per hour of suspension S with a temperature of 7.4° C. were pumped into the distributor space of a first hydraulic wash column which was already in the steady operating state, in order to subject it to a purifying removal process therein.

A correspondingly remaining residual steam of suspension S flowed into a heated collecting vessel with pumped circulation. Also supplied to this collecting vessel was the mother liquor removed in the first hydraulic wash column. In addition, the acrylic acid crystals of the suspension S supplied thereto were melted again in the collecting vessel by corresponding heat supply, such that a startup liquid AT with a temperature of 18° C. could be withdrawn from the collecting vessel. The entire mass flow thereof was first recycled into the condensation column above the side draw withdrawal of the crude acrylic acid. In this way, both a startup liquid AT and a suspension S were available, with which a second hydraulic wash column could be put into operation, the design of which, apart from the pressure difference manometer M3 which had not been installed, corresponded to that in FIG. 2 of this document.

The internal diameter D of the circular cylindrical process space (B) was 1400 mm. The thickness of the outer wall was 10 mm. The material of manufacture was stainless steel (DIN material 1.4571). The length L of the process space (B) was 1500 mm (measured from the upper edge of the bladed disk used as the removal device (16)).

The process space comprised 54 filter tubes (6) of identical design (manufactured from the same material as the outer wall). The wall thickness of the circular cylindrical filter tubes (6) was 5 mm. The external filter tube diameter was 48 mm. The total length of one filter tube (6) was 1497 mm (including displacer (38)). 60 mm of this were accounted for by the height of the filters F (6), which extended over the entire filter tube circumference. The upper edge of a filter F (7) was at a filter tube length of 1182 mm (measured from the top downward). The length of the filter tube displacer (38) extended to 250 mm. The central cylindrical displacer body (43) in the process space (B) had an external diameter of 350 mm. It was connected to the end B (32) and, as a result, configured so as to be stationary (i.e. nonrotating). The arrangement (distribution) of the filter tubes (6) in the end B (32) and of the passages U (26) corresponded to the teaching of EP-A 1 448 282. The number of passages U (26) was 78, the length thereof (from the distributor space to the process space) was 600 mm. They have a circular cross section which is constant over the length thereof, the diameter of which was a uniform 83 mm. The height of the distributor space (A) was 1700 mm.

First, the hydraulic wash column (0) was filled completely with the startup liquid AT at 18° C. from the collecting vessel (melt circuit (31)+process space (B)+distributor space (A)+ the delivery connections E2 (34), C2 (36), C1 (35)+the delivery pump P3 (13)). The filling was effected via the flush liquid supply space (40) through the flush tubes (42).

Subsequently, the delivery pump P3 (13) was put into operation and its speed was adjusted such that it sucked in a flow of 30 000 kg/h of the startup liquid AT through the delivery connection C1 (35) and conveyed it in the following circuit: suction side of the delivery pump P3—pressure side of the delivery pump P3—delivery connection C2 (36)— distributor space (A)—process space (B)—filter F (7)—filter tubes (6)—delivery connection C1 (35) (outlet A (3) was closed).

Then (with the outlet A (3) still closed and the removal device (16) (bladed disk) not in operation and melt circuit (31) not in operation) the delivery pump P2 (8) was put into operation and this was used to withdraw from the buffer vessel, through a withdrawal stub, 25 000 kg/h of the suspension S of acrylic acid crystals in mother liquor, which were pumped at a temperature of 7.4° C. via the delivery connections E1 (33), E2 (34), in addition to the abovementioned flow of 30 000 kg/h, into the distributor space (A) of the hydraulic wash column (0). With delivery pumps P2 (8) and P3 (13) thus put into operation, the crystal bed developed in the process space of the hydraulic wash column (0) (18 750 kg/h of waste liquor flowed out of the outlet (2) of the wash column apparatus). This was accompanied by a rise, in parallel at first, in the pressures measured with the membrane manometers M1 (pressure in the distributor space (A)) and M2 (pressure in the crystal melt space (C)). The total waste liquor flow which flowed through the filters F (7) was 45 200 l/h, which corresponded to a (mean) filter superficial velocity of 92 m³/(m²·h).

After $t_S$=24 min (calculated from commencement of the startup of the delivery pump P2 (8)), the pressure $P_K$ detected with the membrane manometer M2 suddenly began to fall, while the pressure $P_V$ detected with the membrane manometer M1 continued to rise, which corresponded to a first fall in the pressure difference $P_D = P_K - P_V$.

Immediately after the pressure change, the delivery pumps P2 (8) and P3 (13) (in that sequence) were switched off and the delivery pump P1 (11) and the rotation of the bladed disk (16) (in that sequence) were put into operation. Subsequently, the delivery pumps P2 (8) with a delivery output of 25 000 kg/h and the delivery pump P3 (13) with a delivery output of 30 000 kg/h were put back into operation, which set the crystal bed including buildup front in downward motion.

Then the heat transferer W (9) was put into operation, as was the metered addition of inhibiting air and pure melt solution having 3% by weight of MEHQ into the melt circuit. By subsequently partially opening the flow through the outlet A (3), starting up the regulation of the temperature of the melt circuit (31) (the corresponding temperature sensor was just beyond the outlet of the heat transferer W in flow direction), starting up the regulation of the position of the buildup front according to WO 2006/111565 (the level of the crystal bed) and starting up the regulation of the wash front position (the corresponding target temperature was 11.2° C.), as described in the description, the separating process was converted to an operating state with stationary position of wash front and buildup front, in which the buildup front was 700 to 1200 mm above the bladed disk (16) and the wash front approx. 100 mm below the lower edge of the filter F (7).

The corresponding flow of suspension S was 30 000 to 32 000 kg/h and the control liquor flow was 0 (delivery pump 3 switched off) to 8000 kg/h.

This operating state could be maintained only over a period of 6.5 hours. Then the bursting disk (48) which had been inserted for pressure safeguarding and was designed for a response pressure of 10 bar fractured. The pressure measurement M1 indicated pressures in the region of <4.5 bar which had been rising up to then but were significantly below the aforementioned response pressure of 10 bar.

An analysis of the pressure conditions present at the time of the bursting disk fracture suggested, as the cause of the fracture, an occlusion in the system for supply of the suspension S into the wash column.

Comparative Example 4

Process for Startup of a Hydraulic Wash Column with L/D=1.07 at a Mean Filter Superficial Velocity of 115 m³/(m²·h)

The same hydraulic wash column as in comparative example 3 was used, except with the difference that it was now additionally equipped with the pressure difference manometer M3. The suspension S was prepared and the startup liquid AT was obtained likewise as described in comparative example 3.

The process for startup differed from the startup process in comparative example 3 merely in that the delivery pump P3 (13) until the time $t_S$ was set to a delivery output of 40 000 kg/h, and the delivery pump P2 (8) to a delivery output of 28 000 kg/h. The total waste liquor flow which flowed through the filters F (7) was thus 56 600 l/h. This corresponds to a (mean) filter superficial velocity of 115 m³/(m²·h).

After 19 minutes (calculated from commencement of startup of the delivery pump P2 (8)), the pressure difference manometer M3 began to indicate an incipient and rising pressure difference. After a further 4 minutes, the time $t_S$ was reached. The pressure $P_K$ detected with the membrane manometer M2 began suddenly to fall, while the pressure $P_V$ detected with the membrane manometer M1 continued to rise, which corresponded to a first fall in the pressure difference $P_D = P_K - P_V$.

Subsequently, operation was continued as in comparative example 3. When the delivery pump P2 (8) was restarted, the delivery output thereof was set to 28 000 kg/h, and the delivery output of the delivery pump P3 (13) to 30 000 kg/h, which set the crystal bed including buildup front in motion.

The separating process put into operation as described was, as in comparative example 3, converted to an operating state with steady-state position of wash front and buildup front, in which the buildup front was 700 to 1200 mm above the bladed disk (16) and the wash front was approx. 100 mm below the lower edge of the filters F (7). The corresponding flow of suspension S was 30 000 to 33 000 kg/h and the control liquor flow was 0 to 8000 kg/h. This operating state could be maintained only over a period of 5 hours. Within this period, the pressure difference manometer M3 displayed an increasing rise in the pressure difference. Then the bursting disk (4) which had been incorporated for pressure safeguarding and was designed for a response pressure of 10 bar fractured. The membrane pressure manometer M1 indicated a pressure in the region of <6 bar which had been rising up to then but was significantly below the aforementioned response pressure of 10 bar.

The plot of the pressure difference monitored with the pressure difference manometer M3 against time shows that, in the course of buildup of the crystal bed, it has grown into the distributor space (A) before the time $t_S$ has been reached. The constant increase in the aforementioned pressure difference suggests advancing occupation of the distributor space (A) and an accompanying increase in compaction of the crystal aggregate present therein.

Example

Inventive Startup of a Hydraulic Wash Column with L/D=1.07 at a Mean Filter Superficial Velocity of 39 m³/(m²·h)

The same hydraulic wash column as in comparative example 4 was used. The suspension S was prepared and the startup liquid AT was obtained as described in comparative example 3.

The process for startup differed from the startup process in comparative example 3 merely in that the delivery pump P3 (13) remained out of operation until the time $t_S$ and the delivery pump P2 (8) was set to a delivery output of 28 000 kg/h. The total waste liquor flow which flowed through the filters F was thus 19 000 l/h. This corresponds to a (mean) filter superficial velocity of 39 m³/(m²·h). With the delivery pump P2 alone running, the crystal bed then built up in the process space. This was discernible, as in the startup processes of the comparative examples, by the rise, at first in parallel, of the pressures measured with the manometers M1 and M2.

After 16 minutes (calculated from the startup of the delivery pump P2 (8)), a rising pressure difference was recorded in the pressure difference membrane manometer M3. After a further 3 minutes, the time $t_S$ was reached. The pressure $P_K$ detected with the membrane manometer M2 began to fall suddenly, while the pressure $P_V$ detected with the membrane manometer M1 continued to rise, which corresponded to a first fall in the pressure difference $P_D = P_K - P_V$.

Subsequently, the procedure was continued as in comparative example 3. When the delivery pump P2 (8) was restarted, its delivery output was set to 30 000 kg/h. In addition to the restart of the delivery pump P2 (8), immediately thereafter, the delivery pump P3 (13) was now also put into operation with a delivery output of 20 000 kg/h, which set the crystal bed including buildup front in motion.

The separating process put into operation as described was subsequently converted, by the measures described in comparative example 3, to an operating state with a steady-state position of wash front and buildup front, in which the buildup front was 700 to 1200 mm above the bladed disk (16) and the wash front was approx. 100 mm below the filters F (7). The corresponding flow of suspension S was 30 000 to 35 000 kg/h and the control liquor flow was 0 to 12 000 kg/h.

Over a period of 21 days, the separating process was executed essentially without disruption.

With commencement of the restart of the delivery pump P2 (8) and the startup of the control liquor pump P3 (18), the pressure difference detected with the pressure difference manometer M3 began to decrease again. Later, the rise in pressure difference observed with the pressure difference manometer M3 until the time $t_s$ was eliminated completely.

The plot of the pressure difference monitored with the pressure difference manometer M3 against time demonstrates that, in the course of buildup of the crystal bed, it has grown into the distributor space (A) before the time $t_s$ has been reached. The subsequent elimination of the rise in pressure difference demonstrates that, in the case of inventive startup, this apparently unavoidable occupation of the distributor space (A) with crystals is, however, reversible.

U.S. provisional Patent Application No. 61/252,181, filed Oct. 16, 2009, and U.S. Provisional Patent Application 61/356078, filed Jun. 18, 2010, are incorporated into the present specification by reference.

In light of the abovementioned teachings, numerous alterations to and deviations from the present invention are possible. It can therefore be assumed that the invention, within the ambit of the appended claims, may be implemented otherwise than as specifically described herein.

The invention claimed is:

1. A process for starting up a separating process for purifying removal of acrylic acid crystals from a suspension S of crystals thereof in mother liquor with an apparatus which comprises a hydraulic wash column which has a process space which is rotationally symmetric with respect to its longitudinal axis running from the top downward and is bounded by a cylindrical outer wall and two opposite ends on the axis of symmetry, in which
  one or more filter tubes extend through the process space from the upper end of the process space parallel to the longitudinal axis thereof, which run toward the lower end of the process space opposite the upper end, and have, in the half of the process space toward the lower end of the process space, at least one filter F which constitutes the only direct connection between the particular filter tube interior and the process space, and are conducted out of the wash column outside the process space,
  the quotient $Q=L/D$ of the distance L between the upper and lower ends of the process space and the diameter D of the process space is 0.3 to 4,
  the lower end of the process space is followed in the downward direction by the crystal melt space of the wash column, a rotatable removal device being integrated between the two spaces and a crystal melt circuit which is conducted through the crystal melt space comprising, outside the crystal melt space,
    a delivery pump P1 which is outside the wash column and has a suction side and a pressure side,
    a first delivery connection G1 which leads from the crystal melt space of the wash column to the suction side of the delivery pump P1,
    a second delivery connection G2 which leads from the pressure side of the delivery pump P1 back into the crystal melt space of the wash column and has an outlet A from the crystal melt circuit with regulable flow, and
    a heat transferer W, through which either the delivery connection (G1 from the crystal melt space to the suction side of the delivery pump P1 or the delivery connection G2 from the pressure side of the delivery pump P1 to the crystal melt space is conducted,
  connected upstream of the upper end of the process space in the upward direction is a distributor space which is separated from the process space at least by one end B which has passages U which lead into the process space on the side of the end B facing the process space and into the distributor space on the side of the end B facing away from the process space,
  a delivery pump P2 which has a suction side and a pressure side and a source QS of the suspension S are present outside the wash column,
    a first delivery connection E1 leading from the source QS to the suction side of the delivery pump P2, and
    a second delivery connection E2 leading from the pressure side of the delivery pump P2 into the distributor space,
  a delivery pump P3 which has a suction side and a pressure side and a source QT of a control liquor are optionally present outside the wash column,
    a first delivery connection C1 leading from the suction side of the pump P3 to the source QT, and
    a second delivery connection C2 leading from the pressure side of the pump P3 into the distributor space and/or into the longitudinal section of the process space between the upper end thereof and the filters F of the filter tubes, and in which, in the course of performance of the separating process, in steady-state operation thereof,
  the pump P2 is used to continuously conduct a stream ST of the suspension S from the source QS through the delivery connections E1, E2 via the distributor space and through the passages U into the process space of the wash column,
  optionally, the pump P3 is used to conduct a stream SL of the control liquor from the source QT through the delivery connections C1, C2 via the distributor space and the passages U and/or directly into the process space of the wash column,
  overall, a stream SM comprising mother liquor and optionally control liquor is conducted as waste liquor stream into the filter tube interior via the filters F of the filter tubes, and out of the wash column via the filter tubes, and this waste liquor stream SM conducted out of the wash column is used as the source QT for the control liquor,
  the conduction of mother liquor and optionally control liquor in the process space of the wash column maintains the development of a crystal bed of acrylic acid crystals which has a buildup front facing the upper end of the process space, at which crystals of the stream ST of the suspension S supplied are added continuously onto the crystal bed,
  the crystal bed is conveyed from the top downward past the filters F toward the rotating removal device by the force which results from the hydraulic flow pressure drop of the conduction of mother liquor and optionally control liquor in the process space,
  the rotating removal device removes acrylic acid crystals from the crystal bed which meets it,
  the stream of the acrylic acid crystals removed is conveyed through the rotating removal device and/or past the rotating removal device into the crystal melt space which follows downstream of the process space in conveying direction of the crystal bed, and melted in the crystal melt circuit conducted through the crystal melt space as a result of introduction of heat with the heat transferer W to give a crystal melt stream, and
  the flow through the outlet A is regulated such that, based on the flow rate of the aforementioned crystal melt stream, proceeding from the crystal melt space, a substream of crystal melt flows as wash melt stream through the rotating removal device and/or past the rotating removal device against the direction of movement of the crystal bed back into the process space, where it ascends within the crystal bed conveyed downward and in doing so washes the mother liquor off the crystals and forces it back, said mother liquor remaining in the crystal bed having been conveyed with the latter under the filters F, which forms, in the longitudinal section of the process space which extends from the filters F to the lower end of the process space, in the crystal bed, a wash front which divides the crystal bed, from the top downward, into a mother liquor zone and into a wash melt zone, and the remaining substream of the aforementioned crystal melt stream leaves the crystal melt circuit through the outlet A, wherein, in the course of startup of the separating process for first development of the crystal bed in the process space, the crystal melt circuit comprising the crystal melt space, and the process space of the previously unfilled wash column, are at first filled with an acrylic acid-comprising startup liquid AT such that the fill height of the startup liquid AT in the process space overtops at least the removal device, then the filling of the wash column is continued by using the pump P2 to conduct a stream ST* of the suspension S from the source QS through the delivery connections E1, E2 via the distributor space and through the passages U into the process space of the wash column and optionally using the pump P3 to conduct a substream of the waste liquor stream SM* conducted out of the wash column through the filter tubes as source QT*, as control liquor stream SL* through the delivery connections C1, C2 via the distributor space and the passages U and/or directly into the process space of the wash column, at least until the time $t_s$ is attained at which the pressure difference $P_D = P_K - P_V$, where $P_K$ is the pressure existing at any desired point in the crystal melt space at a particular time in the supply of the stream ST* and $P_V$ is the pressure which exists at the same time at any desired point in the distributor space, no longer rises or remains constant as a function of the duration of the supply of the stream ST*, but decreases suddenly, with the proviso that until a time $t_s$, the mean superficial velocity on the filters F, calculated as the arithmetic mean of the total waste liquor flow SM* which flows at the particular time through the filters F of the filter tubes during the supply of the stream ST*, divided by the total area of all filters F, is not more than 80 m³/(m²·h), the acrylic acid-comprising startup liquid AT is one from which, in the course of cooling until crystallization sets in, the crystals which form in the course of crystallization are acrylic acid crystals, and between the crystal formation temperature $T^{KB}$, reported in degrees Celsius, of these acrylic acid crystals in the startup liquid AT and the temperature $T^S$, reported in degrees Celsius, of the suspension S of the stream ST*, the following relationship is satisfied:

$T^{KB} \leq T^S + 15°$ C.

2. The process according to claim 1, wherein the mean superficial velocity on the filters F until the time $t_S$ is at least 5 m³/(m²·h).

3. A process according to either of claims 1 and 2, wherein the distance L is ≧0.5 m.

4. A process according to claim 1, wherein the distance L is ≦5 m.

5. A process according to claim 1, wherein $T^{KB}$ is not more than 20° C. below $T^S$.

6. A process according to claim 1, wherein the startup liquid AT is mother liquor removed from the suspension S.

7. A process according to claim 1, wherein the startup liquid AT is that liquid from which the suspension S is obtained by cooling.

8. A process according to claim 1, wherein, at least over 50% of the period calculated from the commencement of supply of the stream ST* of the suspension S until the time $t_S$ is reached, the superficial velocity on the filters F which exists at the particular time is not more than 80 m³/(m²·h).

9. A process according to claim 1, wherein, over the entire period calculated from the commencement of supply of the stream ST* of the suspension S until the time $t_s$ is reached, the superficial velocity on the filters F which exists at the particular time is not more than 80 m³/(m²·h).

10. A process according to claim 1, wherein, at least over 50% of the period calculated from the commencement of supply of the stream ST* of the suspension S until the time $t_s$ is reached, the superficial velocity on the filters F which exists at the particular time is at least 5 m³/(m²·h) or at least 10 m³/(m²·h).

11. A process according to claim 1, wherein, over the entire period calculated from the commencement of supply of the stream ST* of the suspension S until the time $t_s$ is reached, the arithmetic mean M of the total flow of liquid supplied to the process space of the wash column, divided by the free cross-sectional area of the process space, is 1 to 30 m³/(m²·h).

12. A process according to claim 1, wherein, at least over 50% of the period calculated from the commencement of supply of the stream ST* of the suspension S until the time $t_s$ is reached, the total flow of liquid supplied to the process space of the wash column at the particular time, divided by the free cross-sectional area of the process space, is 1 to 30 m³/(m²·h) or 5 to 25 m³/(m²·h).

13. A process according to claim 1, wherein content of acrylic acid in the suspension S is ≧70% by weight.

14. A process according to claim 1, wherein the degree of crystallization of the suspension S is ≧0.10.

15. A process according to claim 1, wherein the longest dimension of the majority of acrylic acid crystals present in the suspension S is 50 to 1600 µm.

16. A process according to claim 1, wherein the orifice ratio OV of the removal device is ≧0.01.

17. A process according to claim 1, wherein the orifice ratio OV of the removal device is ≦0.9.

18. A process according to claim 1, wherein the removal device is a bladed disk having passage orifices.

19. A process according to claim 1, wherein the crystal melt circuit and the process space of the previously unfilled wash column are at first filled with an acrylic acid-comprising startup liquid AT such that the fill height of the startup liquid AT in the process space overtops at least the filters F.

20. A process according to claim 1, wherein the temperature of the suspension S is −25 to +14° C.

21. A process according to claim 1, wherein the mother liquor present in the suspension S comprises ≧70% by weight of acrylic acid.

22. A process according to claim 1, wherein a substream of the waste liquor stream SM* conducted out of the wash column through the filter tubes as source QT* is conducted with the pump P3 as control liquor stream SL* through the delivery connections C1, C2 via the distributor space and through the passages U into the process space of the wash column.

23. A process according to claim 1, wherein both the pressure $P_K$ and the pressure $P_V$ are measured during the startup.

24. A process according to claim 1, wherein the pressure difference $P_D$ is determined with a pressure difference manometer.

25. A process according to claim 1, wherein, after the time $t_s$, the melt circuit and the removal device are put into operation and the flow through the outlet A is opened, and a molecular oxygen-comprising gas is metered into the melt circuit, by introducing the molecular oxygen-comprising gas into a substream of the melt circuit, and then supplying the substream comprising the molecular oxygen back to the melt circuit.

26. A process according to claim 1, wherein the number of filter tubes in the hydraulic wash column is 3 to 200.

27. A process according to claim 1, wherein the suspension S has the following contents:
≧70% by weight of acrylic acid,
up to 15% by weight of acetic acid,
up to 5% by weight of propionic acid,
up to 5% by weight of low molecular weight aldehydes,
up to 3% by weight of diacrylic acid, and
tip to 25% by weight of water.

28. A separating process for purifying removal of acrylic acid crystals from a suspension S of crystals thereof in mother liquor with an apparatus which comprises a hydraulic wash column, wherein the separating process has been put into operation by a process of claim 1.

29. A process according to claim 28, which is followed by a further process in which removed and molten acrylic acid crystals are subjected to a polymerization with acrylic acid itself or other, at least monoethylenically unsaturated compounds.

30. A process for starting up a separating process for purifying removal of acrylic acid crystals from a suspension S of crystals thereof in mother liquor with an apparatus which comprises a hydraulic wash column which has a process space which is rotationally symmetric with respect to its longitudinal axis running from the top downward and is bounded by a cylindrical outer wall and two opposite ends on the axis of symmetry, in which
one or more filter tubes extend through the process space from the upper end of the process space parallel to the longitudinal axis thereof, which run toward the lower end of the process space opposite the upper end, and have, in the half of the process space toward the lower end of the process space, at least one filter F which constitutes the only direct connection between the particular filter tube interior and the process space, and are conducted out of the wash column outside the process space,
the quotient Q=L/D of the distance L between the upper and lower ends of the process space and the diameter D of the process space is 0.3 to 4,
the lower end of the process space is followed in the downward direction by the crystal melt space of the wash column, a rotatable removal device being integrated between the two spaces and a crystal melt circuit which is conducted through the crystal melt space comprising, outside the crystal melt space,
a delivery pump P1 which is outside the wash column and has a suction side and a pressure side,
a first delivery connection G1 which leads from the crystal melt space of the wash column to the suction side of the delivery pump P1,
a second delivery connection G2 which leads from the pressure side of the delivery pump P1 back into the crystal melt space of the wash column and has an outlet A from the crystal melt circuit with regulable flow, and
a heat transferer W, through which either the delivery connection G1 from the crystal melt space to the suction side of the delivery pump P or the delivery connection G2 from the pressure side of the delivery pump P1 to the crystal melt space is conducted,
connected upstream of the upper end of the process space in the upward direction is a distributor space which is separated from the process space at least by one end B which has passages U which lead into the process space on the side of the end B facing the process space and into the distributor space on the side of the end B facing away from the process space,
a delivery pump P2 which has a suction side and a pressure side and a source QS of the suspension S are present outside the wash column,
a first delivery connection E1 leading from the source QS to the suction side of the delivery pump P2, and
a second delivery connection E2 leading from the pressure side of the delivery pump P2 into the distributor space,
a delivery pump P3 which has a suction side and a pressure side and a source QT of a control liquor are optionally present outside the wash column,
a first delivery connection C1 leading from the suction side of the pump P3 to the source QT, and
a second delivery connection C2 leading from the pressure side of the pump P3 into the distributor space and/or into the longitudinal section of the process space between the upper end thereof and the filters F of the filter tubes,
and in which, in the course of performance of the separating process, in steady-state operation thereof,
the pump P2 is used to continuously conduct a stream ST of the suspension S from the source QS through the delivery connections E1, E2 via the distributor space and through the passages U into the process space of the wash column,
optionally, the pump P3 is used to conduct a stream SL of the control liquor from the source QT through the delivery connections C1, C2 via the distributor space and the passages U and/or directly into the process space of the wash column,
overall, a stream SM comprising mother liquor and optionally control liquor is conducted as waste liquor stream into the filter tube interior via the filters F of the filter tubes, and out of the wash column via the filter tubes, and this waste liquor stream SM conducted out of the wash column is used as the source QT for the control liquor,
the conduction of mother liquor and optionally control liquor in the process space of the wash column maintains the development of a crystal bed of acrylic acid crystals which has a buildup front facing the upper end of the process space, at which crystals of the stream ST of the suspension S supplied are added continuously onto the crystal bed,
the crystal bed is conveyed from the top downward past the filters F toward the rotating removal device by the force which results from the hydraulic flow pressure drop of the conduction of mother liquor and optionally control liquor in the process space,
the rotating removal device removes acrylic acid crystals from the crystal bed which meets it,
the stream of the acrylic acid crystals removed is conveyed through the rotating removal device and/or past the rotating removal device into the crystal melt space which follows downstream of the process space in conveying direction of the crystal bed, and melted in the crystal melt circuit conducted through the crystal melt space as a result of introduction of heat with the heat transferer W to give a crystal melt stream, and
the flow through the outlet A is regulated such that, based on the flow rate of the aforementioned crystal melt stream, proceeding from the crystal melt space, a substream of crystal melt flows as wash melt stream through the rotating removal device and/or past the rotating removal device against the direction of movement of the crystal bed back into the process space, where it ascends within the crystal bed conveyed downward and in doing so washes the mother liquor off the crystals and forces it back, said mother liquor remaining in the crystal bed having been conveyed with the latter under the filters F, which forms, in the longitudinal section of the process space which extends from the filters F to the lower end of the process space, in the crystal bed, a wash front which divides the crystal bed, from the top downward, into a mother liquor zone and into a wash melt zone, and the remaining substream of the aforementioned crystal melt stream leaves the crystal melt circuit through the outlet A, wherein, in the course of startup of the separating process for first development of the crystal bed in the process space, the crystal melt circuit comprising the crystal melt space, and the process space of the previously unfilled wash column, are at first filled with an acrylic acid-comprising startup liquid AT such that the fill height of the startup liquid AT in the process space overtops at least the removal device, then the filling of the wash column is continued by using the pump P2 to conduct a stream ST* of the suspension S from the source QS through the delivery connections E1, E2 via the distributor space and through the passages U into the process space of the wash column and optionally using the pump P3 to conduct a substream of the waste liquor stream SM* conducted out of the wash column through the filter tubes as source QT*, as control liquor stream SL* through the delivery connections C1, C2 via the distributor space and the passages U and/or directly into the process space of the wash column, at least until the time $t_s$ is attained at which the pressure difference $P_D = P_K - P_V$, where $P_K$ is the pressure existing at any desired point in the crystal melt space at a particular time in the supply of the stream ST* and $P_V$ is the pressure which exists at the same time at any desired point in the distributor space, no longer rises or remains constant as a function of the duration of the supply of the stream ST*, but decreases suddenly, with the proviso that until a time $t_S$, the mean superficial velocity on the filters F, calculated as the arithmetic mean of the total waste liquor flow SM* which flows at the particular time through the filters F of the filter tubes during the supply of the stream ST*, divided by the total area of all filters F, is not more than 80 m³/(m²·h), the acrylic acid-comprising startup liquid AT is one from which, in the course of cooling until crystallization sets in, the crystals which form in the course of crystallization are acrylic acid crystals, and between the crystal formation temperature $T^{KB}$, reported in degrees Celsius, of these acrylic acid crystals in the startup liquid AT and the temperature $T^S$, reported in degrees Celsius, of the suspension S of the stream ST*, the following relationship is satisfied:

$T^{KB} \leq T^S + 15°$ C.

wherein the mean superficial velocity on the filters F until the time $t_S$ is at least 5 m³/(m²·h),
wherein the distance L is $\geq 0.5$ m,
wherein the distance L is $\leq 5$ m, and
wherein $T^{KB}$ is not more than 20° C. below $T^S$.

31. A process according to claim 30, wherein the startup liquid AT is mother liquor removed from the suspension S.

32. A process according to claim 30, wherein the startup liquid AT is that liquid from which the suspension S is obtained by cooling.

33. A process according to claim 30, wherein, at least over 50% of the period calculated from the commencement of supply of the stream ST* of the suspension S until the time $t_S$ is reached, the superficial velocity on the filters F which exists at the particular time is not more than 80 m³/(m²·h).

34. A process according to claim 30, wherein, over the entire period calculated from the commencement of supply of the stream ST* of the suspension S until the time $t_s$ is reached, the superficial velocity on the filters F which exists at the particular time is not more than 80 m³/(m²·h).

35. A process according to claim 30, wherein, at least over 50% of the period calculated from the commencement of supply of the stream ST* of the suspension S until the time $t_s$ is reached, the superficial velocity on the filters F which exists at the particular time is at least 5 m³/(m²·h) or at least 10 m³/(m²·h).

36. A process according to claim 30, wherein, over the entire period calculated from the commencement of supply of the stream ST* of the suspension S until the time $t_s$ is reached, the arithmetic mean M of the total flow of liquid supplied to the process space of the wash column, divided by the free cross-sectional area of the process space, is 1 to 30 m³/(m²·h).

37. A process according to claim 30, wherein, at least over 50% of the period calculated from the commencement of supply of the stream ST* of the suspension S until the time $t_s$ is reached, the total flow of liquid supplied to the process space of the wash column at the particular time, divided by the free cross-sectional area of the process space, is 1 to 30 m³/(m²·h) or 5 to 25 m³/(m²·h).

38. A process according to claim 30, wherein content of acrylic acid in the suspension S is $\geq 70\%$ by weight.

39. A process according to claim 30, wherein the degree of crystallization of the suspension S is $\geq 0.10$.

40. A process according to claim 30, wherein the longest dimension of the majority of acrylic acid crystals present in the suspension S is 50 to 1600 µm.

41. A process according to claim 30,
wherein, at least over 50% of the period calculated from the commencement of supply of the stream ST* of the suspension S until the time $t_S$ is reached, the superficial velocity on the filters F which exists at the particular time is not more than 80 m³/(m²·h),
wherein, at least over 50% of the period calculated from the commencement of supply of the stream ST* of the suspension S until the time $t_s$ is reached, the superficial velocity on the filters F which exists at the particular time is at least 5 m³/(m²·h) or at least 10 m³/(m²·h),
wherein, at least over 50% of the period calculated from the commencement of supply of the stream ST* of the suspension S until the time $t_s$ is reached, the total flow of liquid supplied to the process space of the wash column at the particular time, divided by the free cross-sectional area of the process space, is 1 to 30 m³/(m²·h) or 5 to 25 m³/(m²·h),
wherein content of acrylic acid in the suspension S is $\geq 70\%$ by weight, and
wherein the degree of crystallization of the suspension S is $\geq 0.10$.

* * * * *